United States Patent
Johnson et al.

(10) Patent No.: US 7,491,533 B2
(45) Date of Patent: Feb. 17, 2009

(54) POLYNUCLEOTIDES ENCODING AN ISOLATED β-ISLET CELL TWO-PORE DOMAIN POTASSIUM CHANNEL

(75) Inventors: Jeffrey D. Johnson, Moraga, CA (US); John F. Palma, San Ramon, CA (US); Anthony C. Schweitzer, Menlo Park, CA (US); John E. Blume, Danville, CA (US)

(73) Assignee: Metabolex, Inc., Hayward, CA (US)

( * ) Notice: Subject to any disclaimer, the term of this patent is extended or adjusted under 35 U.S.C. 154(b) by 46 days.

(21) Appl. No.: 11/367,182

(22) Filed: Mar. 3, 2006

(65) Prior Publication Data
US 2006/0148037 A1 Jul. 6, 2006

Related U.S. Application Data

(62) Division of application No. 10/459,190, filed on Jun. 10, 2003, now Pat. No. 7,053,180.

(60) Provisional application No. 60/387,642, filed on Jun. 10, 2002.

(51) Int. Cl.
*C12N 5/00* (2006.01)
*C12N 15/09* (2006.01)
*C12N 1/00* (2006.01)
*C07H 21/04* (2006.01)
*C07K 14/435* (2006.01)

(52) U.S. Cl. .............. 435/325; 435/320.1; 435/252.3; 536/23.5; 530/350

(58) Field of Classification Search ................ None
See application file for complete search history.

(56) References Cited

U.S. PATENT DOCUMENTS

| 5,744,594 | A | 4/1998 | Adelman et al. |
| 6,309,855 | B1 | 10/2001 | Duprat et al. |
| 6,680,180 | B1 | 1/2004 | Jegla |
| 2002/0173636 | A1 | 11/2002 | Chen |

FOREIGN PATENT DOCUMENTS

| JP | 2002-233369 A | 8/2002 |
| WO | WO 02/12340 A2 | 2/2002 |
| WO | WO 02/12340 A3 | 2/2002 |
| WO | WO 02/053730 A1 | 7/2002 |

OTHER PUBLICATIONS

Ashcroft, Frances, M.; "Ion Channels and Disease"; 2000, *Academic Press*, pp. 155-156.
Bork, Peer and Amos Bairoch; "Go hunting in sequence databases but watch out for the traps"; 1996, *Trends Genet.*, vol. 12, No. 10, pp. 425-427.
Bork, Peer; "Powers nad pitfalls in sequence analysis: the 70% hurdle"; 2000, *Genome Res.*, vol. 10, No. 4, pp. 398-400.
Brenner, Steven E.; "Errors in genome annotation"; 1999, *Trends Genet.*, vol. 15, No. 4, pp. 132-133.
Doerks, Tobias et al.; "Protein annotation: detective work for function prediction"; 1998, *Trends Genet.*, vol. 14, No. 6, pp. 248-250.
Girard, Christophe et al.; "Genomic and Functional Characteristics of Novel Human Pancreatic 2P Domain $K^+$ Channels"; 2001, *Biochemical and Biophysical Research Communications*, vol. 282, pp. 249-256.
Han, Jaehee et al.; "Functional properties of four splice variants of a human pancreatic tandem-pore $K^+$ channel, TALK-1"; 2003, *Am. J. Physiol. Cell Physiol.*, vol. 285, No. 3, pp. C529-C538.
Huopio, H. et al.; "$K_{ATP}$ channels and insulin secretion disorders"; 2002, *Am. J. Physiol Endocrinol. Metab.*, vol. 283, No. 2, pp. E207-E216.
Ketchem, Karen A. et al.; "A new family of outwardly rectifying potassium channel proteins with two pore domains in tandem"; 1995, *Nature*, vol. 376, pp. 690-695.
Koster, J. C. et al.; "Hyperinsulinism induced by targeted suppression of beta cell $K_{ATP}$ channels"; 2002, *Proc. Natl. Acad. Sci. U.S.A.*, vol. 99, No. 26, pp. 16992-16997.
Kunkel, Maya T. et al.; "Mutants of a Temperature-Sensitive Two-P Domain Potassium Channel"; 2000, *The Journal of Neuroscience*, vol. 20, No. 20, pp. 7517-7524.
Lehmann-Horn, Frank and Karin Jurkat-Rott; "Voltage-Gated Ion Channels and Hereditary Disease"; 1999, *Physiological Reviews*, vol. 79, No. 4, pp. 1317-1372.
Lesage, Florian et al.; "Molecular and functional properties of two-pore-domain potassium channels"; 2000, *Am J Physiol Renal Physiol*, vol. 279, pp. F793-F801.
Ngo, J. Thomas et al.; "Computational Complexity, Protein Structure Prediction and the Levinthal Paradox" In: *The Protein Folding Problem and Tertiary Structure Prediction*, (K. Merz, Jr. and S. Le Grand, eds.), pp. 492-495, 1994.
Skolnick, Jeffrey and Jacquelyn S. Fetrow; "From genes to protein structure and function: novel applications of computational approaches in the genomic era"; 2000, *TIBTECH*, vol. 18, pp. 34-39.
Smith, Temple F. and Xiaolin Zhang; "The challenges of genome sequence annotation or 'The devil is in the details'"; 1997, *Nature Biotechnology*, vol. 15, pp. 1222-1223.
Wells, James A.; "Additivity of Mutational Effects in Proteins"; 1990, *Biochemistry*, vol. 29, No. 37, pp. 8509-8517.
Williams, S.; "Direct Submission"; Accession AL136087, 2 pages, Sep. 5, 2000.
Williams, S.; "Direct Submission"; Accession CAC07336, 2 pages, Sep. 5, 2000.
Zhou, Yun-Ping et al.; "Overexpression of Repressive cAMP Response Element Modulators in High Glucose and Fatty Acid-treated Rat Islets: A common Mechanism for Glucose Toxicity and Lipotoxicity?"; 2003, *The Journal of Biological Chemistry*, vol. 278, No. 51, pp. 51316-51323.

*Primary Examiner*—Bridget E Bunner
(74) *Attorney, Agent, or Firm*—Townsend and Townsend and Crew LLP

(57) ABSTRACT

The present invention provides polynucleotides encoding potassium channels as well as methods of using the potassium channels to treat and diagnose diabetes and a predisposition for diabetes.

5 Claims, 10 Drawing Sheets

Polypeptide sequence of human BIK

```
  1  MPSAGLCSCW GGRVLPLLLA YVCYLLLGAT IFQLLERQAE AQSRDQFQLE
 51  KLRFLENYTC LDQWAMEQFV QVIMEAWVKG VNPKGNSTNP SNWDFGSSFF
101  FAGTVVTTIG YGNLAPSTEA GQVFCVFYAL LGIPLNVIFL NHLGTGLRAH
151  LAAIERWEDR PRRSQVLQVL GLALFLTLGT LVILIFPPMV FSHVEGWSFS
201  EGFYFAFITL STIGFGDYVV GTDPSKHYIS VYRSLAAIWI LLGLAWLALI
251  LPLGPLLHR CCQLWLLSRG LGVKDGEASD PSGLPRPQKI PISA
```

*FIGURE 1*

|            |                                    |
|------------|------------------------------------|
|            | 10                 20            30 |
| h_IC_TASK.pep | M P S A G L C S C W G G R V L P L L L A Y V C Y L L L G A T |
| r_ICTASK.pep  | M P R A G V C S C W G G Q V L P L L L A Y I C Y L L L G A T |
|            | M P   A G . C S C W G G   V L P L L L A Y . C Y L L L G A T |

|            | 40                 50            60 |
|------------|------------------------------------|
| h_BIK.pep  | I F Q L L E R Q A E A Q S R D Q F Q L E K L R F L E N Y T C |
| r_BIK.pep  | I F Q R L E K Q A E A Q S R D Q F Q L E K L R F L E N Y T C |
|            | I F Q   L E . Q A E A Q S R D Q F Q L E K L R F L E N Y T C |

|            | 70                 80            90 |
|------------|------------------------------------|
| h_BIK.pep  | L D Q W A M E Q F V Q V I M E A W V K G V N P K G N S T N P |
| r_BIK.pep  | L D Q Q A L E Q F V Q V I L E A W V K G V N P K G N S T N P |
|            | L D Q   A   E Q F V Q V I   E A W V K G V N P K G N S T N P |

|            | 100                110           120 |
|------------|------------------------------------|
| h_BIK.pep  | S N W D F G S S F F F A G T V V T T I G Y G N L A P S T E A |
| r_BIK.pep  | S N W D F G S S F F F A G T V V T T I G Y G N L A P S T E A |
|            | S N W D F G S S F F F A G T V V T T I G Y G N L A P S T E A |

|            | 130                140           150 |
|------------|------------------------------------|
| h_BIK.pep  | G Q V F C V F Y A L L G I P L N V I F L N H L G T G L R A H |
| r_BIK.pep  | G Q V F C V F Y A L M G I P L N V V F L N H L G T G L R A H |
|            | G Q V F C V F Y A L   G I P L N V . F L N H L G T G L R A H |

|            | 160                170           180 |
|------------|------------------------------------|
| h_BIK.pep  | L A A I E R W E D R P R R S Q V L Q V L G L A L F L T L G T |
| r_BIK.pep  | L T T L D R W E D H P R H S Q L L Q V L G L A L F L T L G T |
|            | L     . . R W E D . P R . S Q . L Q V L G L A L F L T L G T |

|            | 190                200           210 |
|------------|------------------------------------|
| h_BIK.pep  | L V I L I F P P M V F S H V E G W S F S E G F Y F A F I T L |
| r_BIK.pep  | L V I L I F P P M F F S H V E G W S F R E G F Y F A F I T L |
|            | L V I L I F P P M   F S H V E G W S F   E G F Y F A F I T L |

|            | 220                230           240 |
|------------|------------------------------------|
| h_BIK.pep  | S T I G F G D Y V V G T D P S K H Y I S V Y R S L A A I W I |
| r_BIK.pep  | S T I G F G D Y V V G T D P S K H Y I A V Y R S L A A I W I |
|            | S T I G F G D Y V V G T D P S K H Y I   V Y R S L A A I W I |

|            | 250                260           270 |
|------------|------------------------------------|
| h_BIK.pep  | L L G L A W L A L I L P L G P L L L H R C C Q L W L L S R G |
| r_BIK.pep  | L L G L A W L A V V L S L G S L L L H R C S R L W Q L I R G |
|            | L L G L A W L A . . L   L G   L L L H R C   L W   L   R G |

|            | 280                290           300 |
|------------|------------------------------------|
| h_BIK.pep  | L G V K D G E A S D P S G L P R P Q K I P I S A |
| r_BIK.pep  | L D V K D G - - A A P G S E P R S Q K I P F S A |
|            | L   V K D G         P         P R   Q K I P   S A |

*FIGURE 2*

ClustalW Formatted Alignments

```
                        10             20             30
h_BIK.chanpep     R V L P L L A Y V C Y L L G A T I L Q L L E R Q A E A Q
h_THIK1.chanpep   R F L L A A L I V L Y L L G G A A V F S A L E L A H E R Q
h_TASK2.chanpep   R G P L L T S A I I F Y L A I G A A I E V L E E P H W K E
h_TWIK1.chanpep     G F L V L G Y L L Y L V F G A V V F S S V E L P Y E D L
h_TASK1.chanpep   R T L A L I V C T F T Y L L V G A A V F D A L E S E P E M I
                  R   L . L . .   .   Y L L . G A A V F   . L E       E 40             50             60
h_BIK.chanpep     S R D Q F Q L E K R F L E N Y T C L D Q W A M E Q F V Q V
h_THIK1.chanpep   A K Q R W E E R L A N L S R G H N - L S R D E L R G F L R H
h_TASK2.chanpep   A K K N Y Y T Q K L H L L K E F P C L G Q E G L D K I L E M
h_TWIK1.chanpep   L R Q E L R K L K R R F L E E H E C L S E Q Q L E Q F L G R
h_TASK1.chanpep   E R Q R L E L R Q L E L R A R Y N - L S E G G Y E E L E R V
                  . R Q .       K L . F L .       C L S     . L E     F L   V 70             80             90
h_BIK.chanpep     I M E A W V K G V N P K G N S I N P S N W D F G S S F F F A
h_THIK1.chanpep   Y E E A T R A C I R V D N - - - V R P R W D F T G A F Y F V
h_TASK2.chanpep   V S D A A G Q G V A I T G N Q T F N - N W N W P N A M I F A
h_TWIK1.chanpep   V L E A S N Y G V S V L S N A S G N W N W D F T S A L F F A
h_TASK1.chanpep   V L R L K P H K A G - - - - - - - V Q W R F A G S F Y F A
                  V   E A       G V   .     N   .       N W D F       A F . F A 100            110            120
h_BIK.chanpep     G T V V T T I G Y G N L A P S T E A G Q V F C V F Y A L L G
h_THIK1.chanpep   G T V V S T I G F G M T T A T V G G K I F L I F Y G L V G
h_TASK2.chanpep   A T V I T T I G Y G N V A K K I P A G R L F C V F Y G L F G
h_TWIK1.chanpep   S T V L S I I G Y G H T V L S D G G K A F C I I Y S V I G
h_TASK1.chanpep     T V I T T I G Y G H A A P S T D G G K V F C M F Y A L L G
                    T V   T T I G Y G   . A P   T . G G K . F C . F Y . L . G 130            140            150
h_BIK.chanpep     I P L N V I F L N H L G T G L R A H L A A I E R W E - - -
h_THIK1.chanpep   C S S I I L F N D F L E R L I T I I A Y I M K S C H Q R Q
h_TASK2.chanpep   V P L C L T W I S A L G K F F G G R A K R L G Q F L T - -
h_TWIK1.chanpep   I P F T L L E L T A V Q R I T V H V T R R P V L Y F H - -
h_TASK1.chanpep   I P L T L V M F Q S L G E R I N T F V R Y L L H R A K R - -
                  I P L T L . F . . L G   R .     .         .

160            170            180
h_BIK.chanpep     - - D R P R R S C - - - - - - - - - - - - - - V L Q V
h_THIK1.chanpep   L R R R G A L P Q E S L K D A G Q C E V D S L A G W K P S V
h_TASK2.chanpep   - - K R G V S L R - - - - - - - - - - - - - - K A Q I
h_TWIK1.chanpep   - I R W G F S K Q - - - - - - - - - - - - - - V V A I
h_TASK1.chanpep   - - G L C M R H A - - - - - - - - - - - - - - E V S M
                  . R G       Q 190            200            210
h_BIK.chanpep     L G L A L F L T L G T L V I L I F L P M V F S H V E G - W S
h_THIK1.chanpep   Y Y V M L I L C T A S I L I S C C A S A M Y T P I E G - W S
h_TASK2.chanpep   T C T V I F I V W G V L V H L V L P P F V E M V T G - W N
h_TWIK1.chanpep   V H A V L L G F V T V S C F F F L A A V F S V L D D W N
h_TASK1.chanpep   A N M V L I G F V S C I S T L C L G A A A F S Y Y L R - W T
                        . V L . .       .       L   I P   A V F S     E G   W .

220            230            240
h_BIK.chanpep     E S E G F Y F A F I T L S T I G F G D Y V V C T   D P S K H
h_THIK1.chanpep   Y F D S L Y F C F V A F S T I G F G D L V S S Q   N A H Y E
h_TASK2.chanpep   Y I E G L Y Y S F I T I S T I G F G D F V A C V   N P S A N
h_TWIK1.chanpep   L L E S F Y F C F I S L S T I G L G D Y V P G E     G Y N Q K
h_TASK1.chanpep   G F Q A Y Y Y C F I T L T T I G F G D Y V A L Q K D Q A L Q
                    F E . Y F C F I T L S T I . G F G D Y V   G 250            260            270
h_BIK.chanpep     Y I S V V R S L A A I W L L G L A W L A L I L
h_THIK1.chanpep   S Q G L Y R F A N F V F I L M G V C C I Y S L F
h_TASK2.chanpep   Y H A L Y R Y F V E L W L Y V L G L A W L S L F V
h_TWIK1.chanpep   F R E L Y K I G I T C Y L L G L I A M L V V I
h_TASK1.chanpep   T Q P Q M V A F S F V Y I L T G L T V I G A F L
                    .   L Y R . . . . I L L G L . . . . . L
```

A
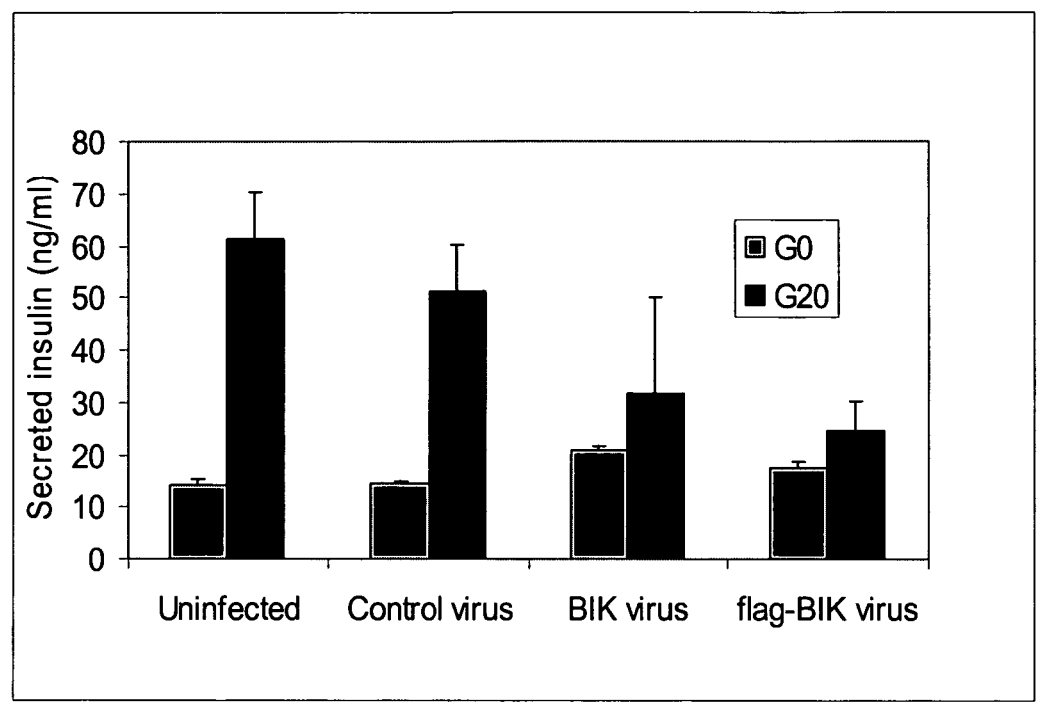
B
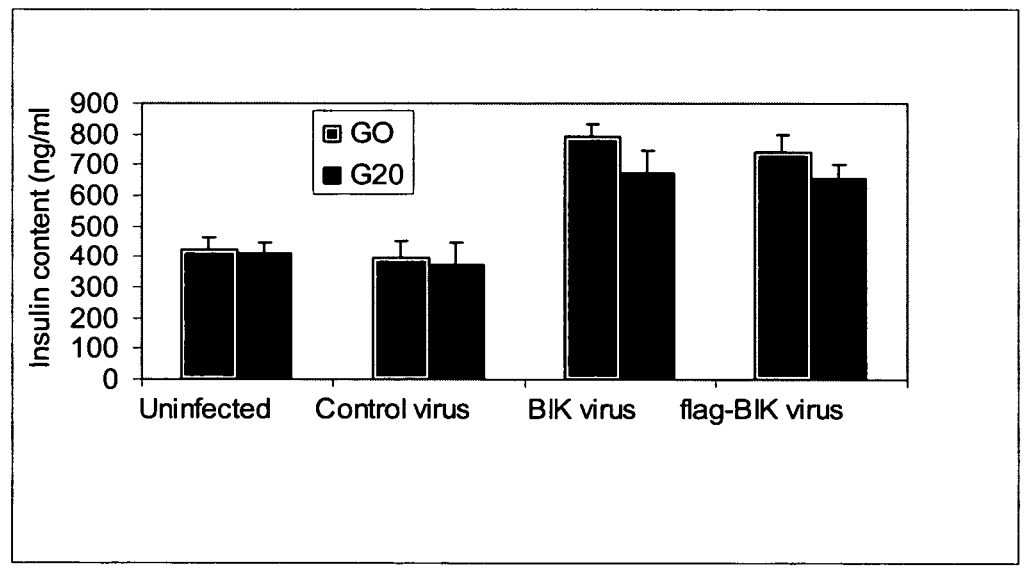
*FIGURE 8*

POLYNUCLEOTIDES ENCODING AN ISOLATED β-ISLET CELL TWO-PORE DOMAIN POTASSIUM CHANNEL

CROSS-REFERENCE TO RELATED APPLICATIONS

The present application is a divisional of U.S. application Ser. No. 10/459,190, filed Jun. 10, 2003, which claims benefit of priority from U.S. Provisional Patent Application No. 60/387,642, filed Jun. 10, 2002, each of which is incorporated by reference for all purposes.

BACKGROUND OF THE INVENTION

Potassium channels set and modulate the electrical potential of the plasma membrane in multiple cell types. In doing so, they play a major role in a number of physiological processes including neuronal excitability and hormone secretion. In the pancreatic beta cell, one important channel involved in setting the membrane potential is Kir6.2, an ATP-sensitive potassium channel. When levels of glucose are low, the concentration of ATP in the cytoplasm of the insulin secreting beta cell is also low. Under these conditions Kir6.2 channels are open, thereby hyperpolarizing the cell membrane. When glucose levels are high, cytoplasmic ATP concentrations also rise and shut off the current through Kir6.2. This depolarizes the plasma membrane and initiates the voltage-dependent opening of L-type $Ca^{++}$ channels (Aguilar-Bryan and Bryan, *Endocr. Rev.* 20:101-135 (1999)).

A number of drugs that act on K+ channels are in use for Type 2 diabetes. The sulphonylurea drugs increase insulin secretion by inhibiting the channel activity of Kir6.2. Sulphonylureas have their activity via interaction with a protein, the sulphoynylurea receptor (SUR1) that associates with Kir6.2 and regulates its activity. Diazoxide is a KATP channel opener that is used clinically for suppressing insulin secretion (ION CHANNELS AND DISEASE (Ashcroft, 2000)). Kir6.2 is found associated with other sulphonylurea receptor proteins (e.g., SUR2A and SUR2B) in other tissues. Mutations in the SUR1 subunit of the KATP channel lead to a syndrome known as Persistent Hyperinsulinemic Hypoglycemia of Infancy (PHHI) that results in constant depolarization of the beta cell plasma membrane and constitutive secretion of insulin.

Channel forming domains are found in all $K^+$ channels. These elements allow for formation of a $K^+$ permeable channel (Pascual, J. M. et al., *Neuron* 14:1055-1063 (1995)). The majority of mammalian $K^+$ channels have just one of these features. A subclass of potassium channels has four transmembrane segments domains and two channel forming domains. This subclass forms a single pore by dimerization. There are at least fourteen such channels in the human genome, more than 11 in *Drosophila* and around 50 in the *C. elegans* genome. Such channels are often "background" or "leak" channels" because they are open at the resting potential and are likely to be important in setting the resting potential and regulating the excitability of cells.

Diabetes mellitus can be divided into two clinical syndromes, Type 1 and Type 2 diabetes mellitus. Type 1, or insulin-dependent diabetes mellitus (IDDM), is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the level required for euglycemia (normal blood glucose level). Although the exact trigger for this immune response is not known, patients with IDDM have high levels of antibodies against pancreatic beta cells. However, not all patients with high levels of these antibodies develop IDDM.

Type 2 diabetes (also referred to as non-insulin dependent diabetes mellitus (NIDDM)) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type 2 diabetes.

Type 2 diabetes is brought on by a combination of poorly understood genetic and acquired risk factors—including a high-fat diet, lack of exercise, and aging. Worldwide, Type 2 diabetes has become an epidemic, driven by increases in obesity and a sedentary lifestyle, widespread adoption of western dietary habits, and the general aging of the populations in many countries. In 1985, an estimated 30 million people worldwide had diabetes—by 2000, this figure had increased 5-fold, to an estimated 154 million people. The number of people with diabetes is expected to double between now and 2025, to about 300 million.

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is the inability of beta cells to produce sufficient insulin to maintain glucose levels. Therefore, an important therapeutic goal in the treatment of diabetes is therefore to increase insulin production. The present invention addresses this and other problems.

BRIEF SUMMARY OF THE INVENTION

The present invention provides isolated polynucleotides encoding a potassium channel comprising a sequence at least 90% identical to SEQ ID NO:10. In some embodiments, the polynucleotide does not encode SEQ ID NO:9. In some embodiments, the potassium channel comprises the sequence displayed in SEQ ID NO: 10. In some embodiments, the potassium channel comprises SEQ ID NO:2. In some embodiments, the polynucleotide comprises SEQ ID NO:1.

Th present invention also provides isolated polynucleotides encoding a potassium channel at least 80% identical to SEQ ID NO:2. In some embodiments, the amino acid of the potassium channel corresponding to amino acid number 277 of SEQ ID NO:2 is glutamate.

Th present invention also provides isolated polynucleotides encoding a potassium channel at least 88% identical to SEQ ID NO:4. In some embodiments, the polynucleotide encodes SEQ ID NO:4. In some embodiments, the polynucleotide comprises SEQ ID NO:3.

The present invention also provides cells transfected with the polynucleotide described above. In some embodiments, the cell is a pancreatic islet cell.

The present invention also provides isolated polypeptides comprising a sequence at least 90% identical to SEQ ID NO:10. In some embodiments, the polypeptide is not SEQ ID NO:9. In some embodiments, the polypeptide comprises a sequence identical to SEQ ID NO:10. In some embodiments, the sequence is displayed in SEQ ID NO:2.

The present invention also provides isolated polypeptide at least 80% identical to SEQ ID NO:2. In some embodiments, the amino acid corresponding to amino acid number 277 of SEQ ID NO:2 is glutamate.

The present invention also provides isolated polypeptides at least 88% identical to SEQ ID NO:4. In some embodiments, the polypeptide comprises SEQ ID NO:4.

The present invention also provides antibodies that specifically binds to SEQ ID NO: 2 or SEQ ID NO:4. In some embodiments, the antibody specifically binds to SEQ ID NO:2. In some embodiments, the antibody binds to SEQ ID NO:4. In some embodiments, the antibody does not bind to SEQ ID NO:9. In some embodiments, the antibody is a monoclonal antibody. In some embodiments, the antibody is a polyclonal antibody.

The present invention also methods of identifying an agent that induces glucose-stimulated insulin production in an animal. In some embodiments, the methods comprise the steps of: (i) contacting an agent to a mixture comprising a polypeptide encoded by a polynucleotide that hybridizes to a sequence encoding SEQ ID NO:2, SEQ ID NO:4 or SEQ ID NO:9 following one wash in 0.2×SSC at 55° C. for 20 minutes; and (ii) selecting an agent that modulates the expression or activity of the polypeptide, thereby identifying an agent that induces glucose-stimulated insulin production in an animal.

In some embodiments, step (ii) comprises selecting an agent that modulates the expression of the polypeptide. In some embodiments, step (ii) comprises selecting an agent that modulates the activity of the polypeptide. In some embodiments, the polypeptide comprises SEQ ID NO:2. In some embodiments, the polypeptide comprises SEQ ID NO:4. In some embodiments, the polypeptide comprises SEQ ID NO:9. In some embodiments, the polypeptide does not comprise SEQ ID NO:9. In some embodiments, the polypeptide comprises SEQ ID NO:10.

In some embodiments, the polypeptide is linked to a solid support. In some embodiments, the agent is linked to a solid support. In some embodiments, the agent is selected by identifying an agent that specifically binds to the polypeptide. In some embodiments, the mixture comprises a cell expressing the polypeptide. In some embodiments, the activity of the polypeptide is determined by a step comprising measuring a change in calcium flux in a cell. In some embodiments, the activity of the polypeptide is determined by a step comprising measuring a change in membrane potential of a cell.

In some embodiments, the cell is an insulin-secreting cell. In some embodiments, the activity of the polypeptide is determined by a step comprising measuring a change in insulin secretion by the cell. In some embodiments, the activity of the polypeptide is determined by the step comprising measuring a change in glucose-stimulated insulin secretion by the cell. In some embodiments, the method further comprising administering the agent to a diabetic animal and testing the animal for increased glucose-stimulated insulin secretion.

The present invention also provides methods of inducing glucose-stimulated insulin production in an animal, the method comprising administering a therapeutically effective amount of the agent selected by the methods described above. In some embodiments, the animal is a human.

DEFINITIONS

"Predisposition for diabetes" occurs in a person when the person is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 $kg/m^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" *Diabetes Care* 25(1): S5-S24 (2002).

A "lean individual," when used to compare with a sample from a patient, refers to an adult with a fasting blood glucose level less than 110 mg/dl or a 2 hour PG reading of 140 mg/dl. A "2 hour PG" refers to the level of blood glucose after challenging a patient to a glucose load containing the equivalent of 75 g anhydrous glucose dissolved in water. The overall test is generally referred to as an oral glucose tolerance test (OGTT). See, e.g., *Diabetes Care*, Supplement 2002, American Diabetes Association: Clinical Practice Recommendations 2002. The level of a polypeptide in a lean individual can be a reading from a single individual, but is typically a statistically relevant average from a group of lean individuals. The level of a polypeptide in a lean individual can be represented by a value, for example in a computer program.

An "β-cell inhibitory potassium channel (BIK) polypeptide," "BIK protein" or "BIK" refers to a potassium channel comprising two channel forming domains, or fragment thereof, that is substantially identical to SEQ ID NO:2, SEQ ID NO:4, SEQ ID NO:9, SEQ ID NO:10 or peptidomimetic compositions with substantially the same activity as SEQ ID NO:2, SEQ ID NO:4, SEQ ID NO:9, or SEQ ID NO:10. BIK comprises two channel forming domains. Channel forming domains are displayed in bold and transmembrane domains are underlined in FIG. 1. Expression of naturally-occurring BIK is typically highly enriched in the pancreas, and more specifically, islet cells.

A "channel forming domain" refers to a portion of a potassium channel that forms a channel in a membrane. Channel forming domains of human BIK are in bold in FIG. 1. Typically, four such domains are combined to form the channel. In cases where the polypeptide comprises one channel-forming domain, typically four polypeptides are required to form the channel. In cases where each polypeptide comprises four transmembrane domains and two channel-forming domains. See, e.g., Ketchum, et al., *Nature* 376: 690-5 (1995).

A "BIK nucleic acid" or "BIK polynucleotide sequence" of the invention is a subsequence or full-length polynucleotide sequence that encodes a BIK polypeptide. Exemplary BIK nucleic acids of the invention include sequences substantially identical to e.g., SEQ ID NO:1, SEQ ID NO:3 and polynucleotides that encode SEQ ID NO:2, SEQ ID NO:4, SEQ ID NO:9, SEQ ID NO:10. In some embodiments, the BIK polynucleotides encode a polypeptide substantially similar to SEQ ID NO:2, wherein amino acid 277 is glutamic acid or SEQ ID NO:9, wherein amino acid 277 is glutamic acid.

"BIK activity" or "potassium channel activity," as used herein, refers to the ability of a protein to set or modulate electrical potential of the plasma membrane of a cell. Activity can be measured, for example, using patch-clamp techniques. Patch-clamp analysis generally involves formation of a high resistance seal between the cell membrane and the glass wall of a micropipette. Current flowing through the ion channels in the membrane is then measured. See, e.g., Ashcroft et al., 2000, supra. One can also use fluorescent dyes or fluorescent resonance energy transfer (FRET) reagents that are sensitive to membrane potential to detect the activity of a channel in a cell. Miller et al., *Eur J. Pharmacol.* 370(2):179-85 (1999); Fedida, et al., *Prog Biophys Mol Biol.* 75(3):165-99 (2000).

An "agonist of BIK" refers to an agent that binds to BIK, stimulates, increases, activates, facilitates, enhances activation, sensitizes or up regulates the activity or expression of BIK.

An "antagonist of BIK" refers to an agent that binds to, partially or totally blocks stimulation, decreases, prevents, delays activation, inactivates, desensitizes, or down regulates the activity or expression of BIK.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the BIK polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a BIK polypeptide, but have one or more peptide linkages optionally replaced by a linkage selected from the group consisting of, e.g., —CH2NH—, —CH2S—, —CH2-CH2-, —CH=CH— (cis and trans), —COCH2-, —CH(OH) CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of BIK or inhibiting or increasing the enzymatic activity of BIK.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) *Nuc. Acids Res.* 12:387-395).

Another example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of BIK expression or of BIK activity are used to refer to inhibitory, activating, or modulating molecules, respectively, identified using in vitro and in vivo assays for BIK expression or BIK activity, e.g., ligands, agonists, antagonists, and their homologs and mimetics. The term "modulator" includes inhibitors and activators. Inhibitors are agents that, e.g., inhibit expression of BIK or bind to, partially or totally block stimulation or enzymatic activity, decrease, prevent, delay activation, inactivate, desensitize, or down regulate the activity of BIK, e.g., antagonists. Activators are agents that, e.g., induce or activate the expression of BIK or bind to, stimulate, increase, open, activate, facilitate, enhance activation or enzymatic activity, sensitize or up regulate the activity of BIK, e.g., agonists. Modulators include naturally occurring and synthetic ligands, antagonists, agonists, small chemical molecules and the like. Such assays for inhibitors and activators include, e.g., applying putative modulator compounds to pancreatic cells or other cells expressing BIK, in the presence or absence of BIK modulators and then determining the functional effects on BIK activity, as described above. Samples or assays comprising BIK that are treated with a potential activator, inhibitor, or modulator are compared to control samples without the inhibitor, activator, or modulator to examine the extent of effect. Control samples (untreated with modulators) are assigned a relative BIK activity value of 100%. Inhibition of BIK is achieved when the BIK activity value relative to the control is about 80%, optionally 50% or 25-1%. Activation of BIK is achieved when the BIK activity value relative to the control is 110%, optionally 150%, optionally 200-500%, or 1000-3000% higher.

BRIEF DESCRIPTION OF THE DRAWINGS

FIG. 1 illustrates the polypeptide sequence encoded by a human cDNA BIK clone (SEQ ID NO:2). The sequences in bold represent the channel-forming domains. The underlined sequences represent the transmembrane domains.

FIG. 2 illustrates a ClustalW alignment of human (SEQ ID NO:2) and rat (SEQ ID NO:4) BIK polypeptide sequences. Consensus sequence=SEQ ID NO:10.

FIG. 3 illustrates a ClustalW alignment of the TM and Pore domains of BIK (SEQ ID NO:11) with the similar domains from THIK1 (SEQ ID NO:12), TASK2 (SEQ ID NO:13), TASK1 (SEQ ID NO:15) and TWIK1 (SEQ ID NO:14). Consensus peptides=SEQ ID NOS:16-22.

FIG. 8 illustrates BIK caused glucose insensitivity and insulin retention in a beta cell line. The mouse glucose responsive beta cell line βHC9 was plated in 12 well plates, and individual wells were either left uninfected or infected (MOI=25) with an adenovirus expressing human BIK (BIK virus), an adenovirus expressing BIK with an N-terminal flag tag (flag-BIK virus) or an adenovirus identical to these two but lacking the BIK (or flag-BIK) coding sequence. 24 h after infection the cells were washed and placed in KRB buffer with 0.1 mM glucose for 40 min. and washed with KRB. The cells were subsequently incubated in KRB contain 0.1 mM (FIG. 8A, light bars) or 20 mM (dark bars) glucose for 1 h. The mass of insulin secreted from the cells (FIG. 8A) was determined by RIA of an aliquot of the buffer exposed to the cells, and the insulin remaining in the cells (Insulin content; FIG. 8B) was determined by RIA after extraction with acid-ethanol. The values for secreted insulin and insulin content are the mean±S.E. of triplicate determinations. Similar results were obtained in a second independent experiment.

DETAILED DESCRIPTION OF THE INVENTION

I. Introduction

Figure 4:
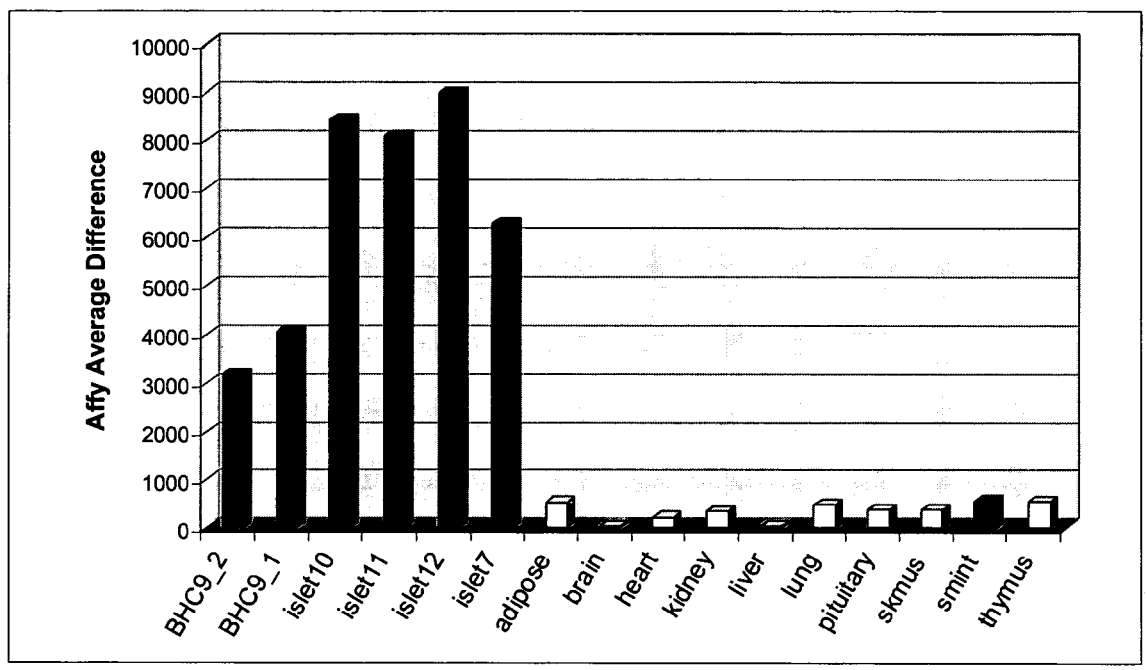
FIG. 4 illustrates mouse islet chip hybridization results demonstrating the islet enrichment of BIK mRNA relative to other tissues. Chips were hybridized with equivalent amounts of cRNA from a pancreatic beta cell line (betaHC9), four sets of isolated mouse islets, as well as the mouse tissues: adipose, brain, heart, kidney, liver, lung, pituitary, skeletal muscle, small intestine and thymus. The Average Difference score reflects the relative abundance of the BIK mRNA in each of the tissues. The Affymetrix GeneChip analysis package called the BIK mRNA Present in betaHC9, all of the islets samples and also in small intestine (at a much lower Average Difference score). The analysis package judged the BIK mRNA to be Absent in all of the other tissues.

The present application demonstrates that, surprisingly, BIK is expressed in higher levels in animals fed a high fat diet and in animals that are diabetic compared to levels in healthy, lean animals. Moreover, expression of BIK is highly enriched in the islet cells of the pancreas, where insulin production occurs. BIK is a $K^+$ channel that maintains the resting potential of cells. The upregulation of BIK observed in islets from diabetic animals or animals predisposed for diabetes demonstrates that BIK upregulation interferes with insulin secretion. Accordingly, antagonizing BIK expression or activity is useful for treating diabetes.

This invention is directed to new polypeptide and polynucleotide sequences, designated BIK sequences, as well as methods of using BIK sequences to diagnose and treat diabetes. The present method also provides methods of identifying modulators of BIK expression and activity. Such modulators are useful for treating type 1 and type 2 diabetes as well as the pathological aspects of such diseases.

II. General Recombinant Nucleic Acid Methods for Use with the Invention

In numerous embodiments of the present invention, nucleic acids encoding a BIK of interest will be isolated and cloned using recombinant methods. Such embodiments are used, e.g., to isolate BIK polynucleotides (e.g., SEQ ID NO:1 or SEQ ID NO:3) for protein expression or during the generation of variants, derivatives, expression cassettes, or other sequences encoding a BIK polypeptide (e.g., SEQ ID NO:2, SEQ ID NO:4, SEQ ID NO:9 or SEQ ID NO:10), to monitor BIK gene expression, for the isolation or detection of BIK sequences in different species, for diagnostic purposes in a patient, e.g., to detect mutations in BIK or to detect expression levels of BIK nucleic acids or BIK polypeptides. In some embodiments, the sequences encoding the BIK of the invention are operably linked to a heterologous promoter. In one embodiment, the nucleic acids of the invention are from any mammal, including, in particular, e.g., a human, a mouse, a rat, etc.

A. General Recombinant Nucleic Acid Methods

This invention relies on routine techniques in the field of recombinant genetics. Basic texts disclosing the general methods of use in this invention include Sambrook et al.,

*Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of BIK (e.g., SEQ ID NO:1 or SEQ ID NO:3), which provides a reference for PCR primers and defines suitable regions for isolating BIK-specific probes. Alternatively, where the sequence is cloned into an expression library, the expressed recombinant protein can be detected immunologically with antisera or purified antibodies made against the BIK of interest.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Pancreatic cells are an example of suitable cells to isolate BIK RNA and cDNA.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific BIK sequences, e.g., the sequences set forth in SEQ ID NO:1 or SEQ ID NO:3. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a BIK polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding a BIK polypeptide of the invention from mammalian tissues can be derived from the sequences provided herein, in particular SEQ ID NO:1 or SEQ ID NO:3, or encoding amino acid sequences within BIK polypeptides, e.g., SEQ ID NO:2 and SEQ ID NO:4. For a general overview of PCR, see, Innis et al. *PCR Protocols: A Guide to Methods and Applications, Academic Press*, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding a BIK polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant BIK can be purified for use in functional assays. Naturally occurring BIK can be purified, e.g., from mammalian (e.g., human) tissue such as pancreatic cells or any other source of a BIK ortholog. Recombinant BIK can be purified from any suitable expression system.

The BIK may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant BIK is purified. For example, proteins having established molecular adhesion properties can be reversibly fused to BIK. With the appropriate ligand, BIK can be selectively adsorbed to a purification column and then freed from the column in a relatively pure form. The fused protein may be then removed by enzymatic activity. Finally BIK could be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Purification of Proteins from Insect Cells

Proteins can also be purified from eukaryotic gene expression systems as described in, e.g., Fernandez and Hoeffler, *Gene Expression Systems* (1999). In some embodiments, baculovirus expression systems are used to isolate BIK proteins or other proteins of the invention. Recombinant baculoviruses are generally generated by replacing the polyhedrin coding sequence of a baculovirus with a gene to be expressed (e.g., a BIK polynucleotide). Viruses lacking the polyhedrin gene have a unique plaque morphology making them easy to recognize. In some embodiments, a recombinant baculovirus is generated by first cloning a polynucleotide of interest into a transfer vector (e.g., a pUC based vector) such that the polynucleotide is operably linked to a polyhedrin promoter. The transfer vector is transfected with wildtype DNA into an insect cell (e.g., Sf9, Sf21 or BT1-TN-5B1-4 cells), resulting in homologous recombination and replacement of the polyhedrin gene in the wildtype viral DNA with the polynucleotide of interest. Virus can then be generated and plaque purified. Protein expression results upon viral infection of insect cells. Expressed proteins can be harvested from cell supernatant if secreted, or from cell lysates if intracellular. See, e.g., Ausubel et al. and Fernandez and Hoeffler, supra.

C. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine (His), glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

IV. Detection of Polynucleotides of the Invention

Those of skill in the art will recognize that detection of expression of BIK polynucleotides has many uses. For example, as discussed herein, detection of BIK alleles or BIK levels in a patient is useful for diagnosing diabetes or a predisposition for at least some of the pathological effects of diabetes. Moreover, detection of gene expression is useful to identify modulators of BIK expression.

A variety of methods of specific DNA and RNA measurement that use nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a BIK polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays,*" *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of, for example, a BIK RNA is measured by quantitating the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), i.e. Gene Chips or microarrays, available from Affymetrix, Inc. in Santa Clara, Calif. can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759. Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment. See, e.g., Schena et al., *Science* 270: 467-470 (1995)) and (Lockhart et al., *Nature Biotech.* 14: 1675-1680 (1996)).

Hybridization specificity can be evaluated by comparing the hybridization of specificity-control polynucleotide sequences to specificity-control polynucleotide probes that are added to a sample in a known amount. The specificity-control target polynucleotides may have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (Shalon et al. PCT publication WO95/35505). In some embodiments, the labels are fluorescent labels with distinguishable emission spectra, such as Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In some embodiments, the polynucleotide probes are labeled with a fluorescent label and measurement of levels and patterns of fluorescence indicative of complex formation is accomplished by fluorescence microscopy, such as confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulavski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *PNAS* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed) *Fundamental Immunology, Third Edition* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1989); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

Single nucleotide polymorphism (SNP) analysis is also useful for detecting differences between alleles of BIK genes (e.g., polynucleotides encoding SEQ ID NOS:2 and 9). BIK-linked SNPs are useful for diagnosis of BIK-linked diseases (e.g., diabetes,) in a patient. SNP analysis is also useful to predict the effectiveness of medications directed to BIK or other diabetes-related targets. For example, if an individual carries at least one allele of a BIK-linked SNP associated with diabetes, the individual is likely predisposed for diabetes. If the individual is homozygous for a disease-linked BIK SNP, the individual is particularly predisposed for diabetes.

Various real-time PCR methods including, e.g., Taqman or molecular beacon-based assays (e.g., U.S. Pat. Nos. 5,210, 015; 5,487,972; Tyagi et al., *Nature Biotechnology* 14:303 (1996); and PCT WO 95/13399 are useful to monitor for the presence of absence of a SNP. Additional SNP detection methods include, e.g., DNA sequencing, sequencing by hybridisation, dot blotting, oligonucleotide array (DNA Chip) hybridization analysis, or are described in, e.g., U.S. Pat. No. 6,177,249; Landegren et al., *Genome Research*, 8:769-776 (1998); Botstein et al., *Am J Human Genetics* 32:314-331 (1980); Meyers et al., Methods in Enzymology 155:501-527 (1987); Keen et al., *Trends in Genetics* 7:5 (1991); Myers et al., *Science* 230:1242-1246 (1985); and Kwok et al., *Genomics* 23:138-144 (1994).

V. Immunological Detection of BIK

In addition to the detection of BIK genes and gene expression using nucleic acid hybridization technology, one can also use immunoassays to detect BIK polypeptides, ligands or other molecules that bind BIK or that modulate BIK activity. Immunoassays can be used to qualitatively or quantitatively analyze BIK. A general overview of the applicable technology can be found in Harlow & Lane, *Antibodies: A Laboratory Manual* (1988).

A. Antibodies to Target Proteins or other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature*, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the BIK sequences disclosed herein is conjugated to a carrier protein and used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their cross-reactivity against non-BIK proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the BIK of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells according to the general protocol outlined by Huse et al., supra.

Once target immunogen-specific antibodies are available, the immunogen can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the BIK or a fragment thereof. This antiserum is selected to have low cross-reactivity against non-BIK proteins and any such cross-reactivity is removed by immunoabsorption prior to use in the immunoassay.

B. Immunological Binding Assays

In some embodiments, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume 37: Antibodies in Cell Biology*, Academic Press, Inc. NY (1993); Stites, supra. Immunological binding assays (or immunoassays) typically utilize a "capture agent" to specifically bind to and often immobilize the analyte (in this case a BIK of the present invention or antigenic subsequences thereof). The capture agent is a moiety that specifically binds to the analyte. In a preferred embodiment, the capture agent is an antibody that specifically binds, for example, a BIK polypeptide of the invention. The antibody may be produced by any of a number of means well known to those of skill in the art and as described above.

Immunoassays also often utilize a labeling agent to bind specifically to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/ protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.,* 111:1401-1406 (1973); and Akerstrom, et al. *J. Immunol.,* 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins or analytes of interest from tissue samples may be either competitive or noncompetitive. Noncompetitive immunoassays are assays in which the amount of captured protein or analyte is directly measured. In one preferred "sandwich" assay, for example, the capture agent (e.g., BIK antibodies) can be bound directly to a solid substrate where it is immobilized. These immobilized antibodies then capture the BIK present in the test sample. The BIK thus immobilized is then bound by a labeling agent, such as a second anti-BIK antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of protein or analyte present in the sample is measured indirectly by measuring the amount of an added (exogenous) protein or analyte (e.g., BIK of interest) displaced (or competed away) from a specific capture agent., e.g. antibodies raised to BIK) by the protein or analyte present in the sample. The amount of immunogen bound to the antibody is inversely proportional to the concentration of immunogen present in the sample. In a particularly preferred embodiment, the antibody is immobilized on a solid substrate. The amount of analyte may be detected by providing a labeled analyte molecule. It is understood that labels can include, e.g., radioactive labels as well as peptide or other tags that can be recognized by detection reagents such as antibodies.

Immunoassays in the competitive binding format can be used for cross-reactivity determinations. For example, the protein encoded by the sequences described herein can be immobilized on a solid support. Proteins are added to the assay and compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of a BIK of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the anti-BIK antibodies specifically bind to BIK on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VI. Identification of Modulators of BIK

Modulators of BIK, i.e. agonists or antagonists of BIK activity or BIK polypeptide or polynucleotide expression, are useful for treating a number of human diseases, including diabetes. Administration of BIK inhibitors can be used to treat diabetic patients or individuals with insulin resistance. Alternatively, activators of BIK can be used to treat diabetic patients or individuals with insulin resistance.

A. Agents that Modulate BIK

The agents tested as modulators of BIK can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to reduce the level of BIK mRNA (e.g. antisense molecules, ribozymes, DNAzymes, small inhibitory RNAs and the like) or the level of translation from an mRNA (e.g., translation blockers such as an antisense molecules that are complementary to translation start or other sequences on an mRNA molecule). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of BIK

A number of different screening protocols can be utilized to identify agents that modulate the level of expression or activity of BIK in cells, particularly mammalian cells, and especially human cells. In general terms, the screening methods involve screening a plurality of agents to identify an agent that modulates the activity of BIK by, e.g., binding to a BIK polypeptide, preventing an inhibitor or activator from binding to BIK, increasing association of an inhibitor or activator with BIK, or activating or inhibiting expression of BIK.

In some embodiments, different BIK polypeptides (e.g., SEQ ID NO:2 and SEQ ID NO:9) are screened in parallel to identify an agent that modulates one BIK variant not a second. For example, a screen can be designed to identify agents that bind or modulate SEQ ID NO:2 but not SEQ ID NO:9 or vice versa.

1. BIK Binding Assays

Preliminary screens can be conducted by screening for agents capable of binding to BIK, as at least some of the agents so identified are likely BIK modulators. Binding assays are also useful, e.g., for identifying endogenous proteins that interact with BIK. For example, antibodies, receptors or other molecules that bind BIK can be identified in binding assays.

Binding assays usually involve contacting a BIK protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to BIK or displacement of labeled substrates. The BIK protein utilized in such assays can be naturally expressed, cloned or synthesized.

In addition, mammalian or yeast two-hybrid approaches (see, e.g., Bartel, P. L. et. al. Methods Enzymol, 254:241 (1995)) can be used to identify polypeptides or other molecules that interact or bind when expressed together in a cell.

2. Expression Assays

Screening for a compound that modulates the expression of BIK are also provided. Screening methods generally involve conducting cell-based assays in which test compounds are contacted with one or more cells expressing BIK, and then detecting an increase or decrease in BIK expression (either transcript, translation product). Assays can be performed with cells that naturally express BIK or in cells recombinantly altered to express BIK.

BIK expression can be detected in a number of different ways. As described infra, the expression level of BIK in a cell can be determined by probing the mRNA expressed in a cell with a probe that specifically hybridizes with a transcript (or complementary nucleic acid derived therefrom) of BIK. Probing can be conducted by lysing the cells and conducting Northern blots or without lysing the cells using in situ-hybridization techniques. Alternatively, BIK protein can be detected using immunological methods in which a cell lysate is probed with antibodies that specifically bind to BIK.

Other cell-based assays involve reporter assays conducted with cells using standard reporter gene assays. These assays can be performed in either cells that do, or do not, express BIK. Some of these assays are conducted with a heterologous nucleic acid construct that includes a BIK promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282:864-869), luciferase, β-galactosidase and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. Modulated promoter expression is monitored by detecting the level of a detectable reporter. A number of different kinds of BIK modulators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of BIK expression levels for a control population (e.g., lean individuals not having or at risk for Type 2 diabetes) or cells (e.g., tissue culture cells not exposed to a BIK modulator). Expression levels can also be determined for cells that do not express BIK as a negative control. Such cells generally are otherwise substantially genetically the same as the test cells.

A variety of different types of cells can be utilized in the reporter assays. Cells that express an endogenous BIK include, e.g., pancreatic cells. Cells that do not endogenously express BIK can be prokaryotic or eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HepG2, COS, CHO and HeLa cell lines. *Xenopus* oocytes can also be used.

Various controls can be conducted to ensure that an observed activity is authentic including running parallel reactions with cells that lack the reporter construct or by not contacting a cell harboring the reporter construct with test compound. Compounds can also be further validated as described below.

3. Activity

Analysis of BIK polypeptide activity is performed according to general biochemical procedures. Such assays include cell-based assays as well as in vitro assays involving purified or partially purified BIK polypeptides or crude cell lysates.

The level of BIK activity in a cell or other sample is determined and compared to a baseline value (e.g., a control value). Activity can be measured based on a crude extract or partially or essentially purified BIK from a sample. Measurement of BIK activity involves measuring cation channel activity, for example, as described in Lesage et al. *Am. J. Physiol. Renal. Physiol.* 279:F793-F801 (2000) and Giratd et al., *Biochem. Biophys. Res. Commun.* 282:249-256 (2001). For example, changes in ion flux may be assessed by determining changes in polarization (i.e., electrical potential) of the cell or membrane expressing the potassium channel comprising a BIK polypeptide. In some embodiments, changes in cellular polarization is monitored by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes or ion sensitive dyes (see, e.g., Vestergarrd-Bogind et al., *J. Membrane Biol.* 88:67-75 (1988); Daniel et al., *J. Pharmacol. Meth.* 25:185-193 (1991); Holevinsky et al., *J. Membrane Biology* 137:59-70 (1994)). Assays for compounds capable of inhibiting or increasing potassium flux through the channel proteins comprising a BIK polypeptide can be performed by application of the compounds to a bath solution in contact with and comprising cells having a channel of the present invention (see, e.g., Blatz et al., *Nature* 323:718-720 (1986); Park, *J. Physiol.* 481:555-570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The ions can be measured in a variety of standard ways. They can be measured directly by concentration changes of the ions, e.g., changes in intracellular concentrations, or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release, intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if BIK is in fact modulated. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty rats etc) or polygenic models of diabetes (e.g., a high fat fed mouse model) can be useful for validating BIK modulation and its effect in a diabetic animal.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., BIK) can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., BIK) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:24). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154

(1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of BIK. Control reactions that measure BIK activity of the cell in a reaction that does not include a potential modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of BIK of the invention can be incubated with one sample of the assay, and the resulting increase in signal resulting from an increased expression level or activity of BIK are determined according to the methods herein. Second, a known inhibitor of BIK can be added, and the resulting decrease in signal for the expression or activity of BIK can be similarly detected. It will be appreciated that modulators can also be combined with activators or inhibitors to find modulators that inhibit the increase or decrease that is otherwise caused by the presence of the known modulator of BIK.

D. Computer-Based Assays

Yet another assay for compounds that modulate the activity of BIK involves computer-assisted drug design, in which a computer system is used to generate a three-dimensional structure of BIK based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions (e.g., the active site) of the structure that have the ability to bind ligands or otherwise be modulated. Similar analyses can be performed on potential receptors or binding partners of BIK and can be used to identify regions of interaction with BIK. These regions are then used to identify polypeptides that bind to BIK.

Once the tertiary structure of a protein of interest has been generated, potential modulators can be identified by the computer system. Three-dimensional structures for potential modulators are generated by entering chemical formulas of compounds. The three-dimensional structure of the potential modulator is then compared to that of BIK to identify binding sites of BIK. Binding affinity between the protein and modulators is determined using energy terms to determine which ligands have an enhanced probability of binding to the protein.

VII. Compositions, Kits and Integrated Systems

The invention provides compositions, kits and integrated systems for practicing the assays described herein using nucleic acids encoding the BIK polypeptides of the invention, or BIK proteins, anti-BIK antibodies, etc.

The invention provides assay compositions for use in solid phase assays; such compositions can include, for example, one or more nucleic acids encoding a BIK immobilized on a solid support, and a labeling reagent. In each case, the assay compositions can also include additional reagents that are desirable for hybridization. Modulators of expression or activity of a BIK of the invention can also be included in the assay compositions.

The invention also provides kits for carrying out the assays of the invention. The kits typically include a probe that comprises an antibody that specifically binds to BIK or a polynucleotide sequence encoding a BIK polypeptide, and a label for detecting the presence of the probe. The kits may include several polynucleotide sequences encoding BIK polypeptides of the invention. Kits can include any of the compositions noted above, and optionally further include additional components such as instructions to practice a high-throughput method of assaying for an effect on expression of the genes encoding the BIK polypeptides of the invention, or on activity of the BIK polypeptides of the invention, one or more containers or compartments (e.g., to hold the probe, labels, or the like), a control modulator of the expression or activity of BIK polypeptides, a robotic armature for mixing kit components or the like.

The invention also provides integrated systems for high-throughput screening of potential modulators for an effect on the expression or activity of the BIK polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Administration and Pharmaceutical Compositions

Modulators of BIK (e.g., antagonists or agonists) can be administered directly to the mammalian subject for modulation of BIK activity in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17$^{th}$ ed. 1985)).

The modulators (e.g., agonists or antagonists) of the expression or activity of BIK, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

The modulators (e.g., agonists or antagonists) of the expression or activity of BIK, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, BIK modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), *Current Therapy In Endocrinology And Metabolism,* 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82(12A): 3U-17U). These studies indicate that modulation of diabetes, among other diseases, can be further improved by the addition of a second agent to the therapeutic regimen. Combination therapy includes administration of a single pharmaceutical dosage formulation that contains a BIK modulator of the invention and one or more additional active agents, as well as administration of a BIK modulator and each active agent in its own separate pharmaceutical dosage formulation. For example, a BIK modulator and a thiazolidinedione can be administered to the human subject together in a single oral dosage composition, such as a tablet or capsule, or each agent can be administered in separate oral dosage formulations. Where separate dosage formulations are used, a BIK modulator and one or more additional active agents can be administered at essentially the same time (i.e., concurrently), or at separately staggered times (i.e., sequentially). Combination therapy is understood to include all these regimens.

One example of combination therapy can be seen in modulating diabetes (or treating diabetes and its related symptoms, complications, and disorders), wherein the BIK modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859,037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose); amylin and amylin derivatives (such as pramlintide, (see, also, U.S. Pat. Nos. 5,902,726; 5,124,314; 5,175,145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

IX. Diagnosis of Diabetes

The present invention also provides methods of diagnosing diabetes or a predisposition of at least some of the pathologies of diabetes or another BIK-related disease. Diagnosis can involve determination of a genotype of an individual (e.g., with SNPs) and comparison of the genotype with alleles known to have an association with the occurrence of diabetes or other BIK-related disease. Determination of BIK genotype is useful to predict the effectiveness of medications as well as a predisposition for diabetes.

Alternatively, diagnosis also involves determining the level of BIK in a patient and then comparing the level to a baseline or range. Typically, the baseline value is representative of BIK in a lean (i.e., non-diabetic and typically healthy) person. As discussed above, variation of levels (e.g., high levels) of BIK from the baseline range indicates that the patient is either diabetic or at risk of developing at least some of the pathologies of diabetes. In some embodiments, the level of BIK are measured by taking a blood, urine or tissue sample from a patient and measuring the amount of BIK in the sample using any number of detection methods, such as those discussed herein. For instance, fasting and fed blood or urine levels can be tested.

In some embodiments, the level of BIK activity or expression in a sample is determined and compared to a baseline value of a lean person or persons. Alternatively, the level of BIK activity or expression is determined for the same individual at more than one time points, e.g., a day, a week and month, a year or longer apart. Modulation of BIK activity or expression between samples indicates the development of diabetes or a predisposition to develop diabetes. In some embodiments, the baseline level and the level in a sample from an individual, or at least two samples from an individual differ by at least about 5%, 10%, 20%, 50%, 75%, 100%, 200%, 500%, 1000% or more. In some embodiments, the sample from the individual is greater by at least one of the above-listed percentages relative to the baseline level. In some embodiments, the sample from the individual is lower by at least one of the above-listed percentages relative to the baseline level. Similarly, the level in a sample taken from an individual some time period after a first sample was taken can be higher or lower than the level in the first sample.

In some embodiments, the level of BIK activity or expression is used to monitor the effectiveness of antidiabetic therapies such as thiazolidinediones, metformin, sulfonylureas and other standard therapies. In some embodiments the activity or expression of BIK will be measured prior to and after treatment of diabetic or insulin resistant patients with antidiabetic therapies as a surrogate marker of clinical effectiveness. For example, the greater the reduction in BIK expression or activity indicates greater effectiveness.

EXAMPLES

The following examples are offered to illustrate, but not to limit the claimed invention.

Example 1

This example illustrates the identification and characterization of BIK.

A K+ channel, BIK (Islet Cell-Two-Pore-Acid-Sensitive-K channel) was identified that has highly enriched expression in the pancreatic islet. Northern blots were performed using a Clontech MTN blot of 2 micrograms of polyA+ RNA from peripheral blood lymphocytes, lung, placenta, small intestine, liver, kidney, spleen, thymus, colon, skeletal muscle, heart, and brain. The blot was probed with identical probe and conditions along with a separate Northern blot loaded with 10 micrograms of human islet total RNA and 2 micrograms each of polyA+ RNA from two preparations of pancreas, testis, adrenal and spleen. A single band of approximately 2.6 kilobases is observed in islet and, to much lesser extent, in pancreas. Since islets constitute 1-5% of total pancreas mass, the enrichment in islets relative to pancreas, reflects that the BIK transcript is found in islets only, and is absent, or much less abundant, in the exocrine (non-islet) portion of the pancreas. Moreover, expression of BIK is increased is diabetic animals and animals fed a high fat diet.

Complementary DNA (cDNA) libraries were generated in pZL1 (Invitrogen) by standard techniques from purified human pancreatic beta cells and were sequenced to the depth of approximately 100,000 clones. Of these, greater than 20 represent independent clones of BIK. One of these clones (bc13011) was sequenced in entirety and encodes a full-length protein having a characteristic two K+ channel-forming domains (FIG. 1). See SEQ ID NOs: 1 and 2. There are four allelic variations between our sequences and the public sequence found in Accession # AL136087: BIK nt 597 is C (AL136087 is T), BIK nt 800 is C (AL136087 is T), BIK nt 934 is A (AL136087 is C), BIK nt 1191 is T (AL136087 is C). The single nucleotide polymorphism (SNP) at nt 934 changes codon 277 from E (glutamate) in BIK to A (alanine) in AL136087.

Subsequently we found two orthologous clones in a cDNA library generated from rat pancreatic islets by standard techniques. One of these clones RIA099-C1, was sequenced in entirety and also encodes a full-length protein. The alignment of the human and rat BIK deduced polypeptide sequences shows that they are 87% identical at the amino acid level (FIG. 2). BIK comprises two channel forming domains and appears to most closely resemble TWIK1 and TWIK2 by dendrogram analysis (MacVector) (FIG. 3).

Numerous mouse clones of BIK were obtained from a mouse islet cDNA library and a GeneChip probe (MBXMU-SISL22471) corresponding to this sequence was synthesized.

Figure 5:
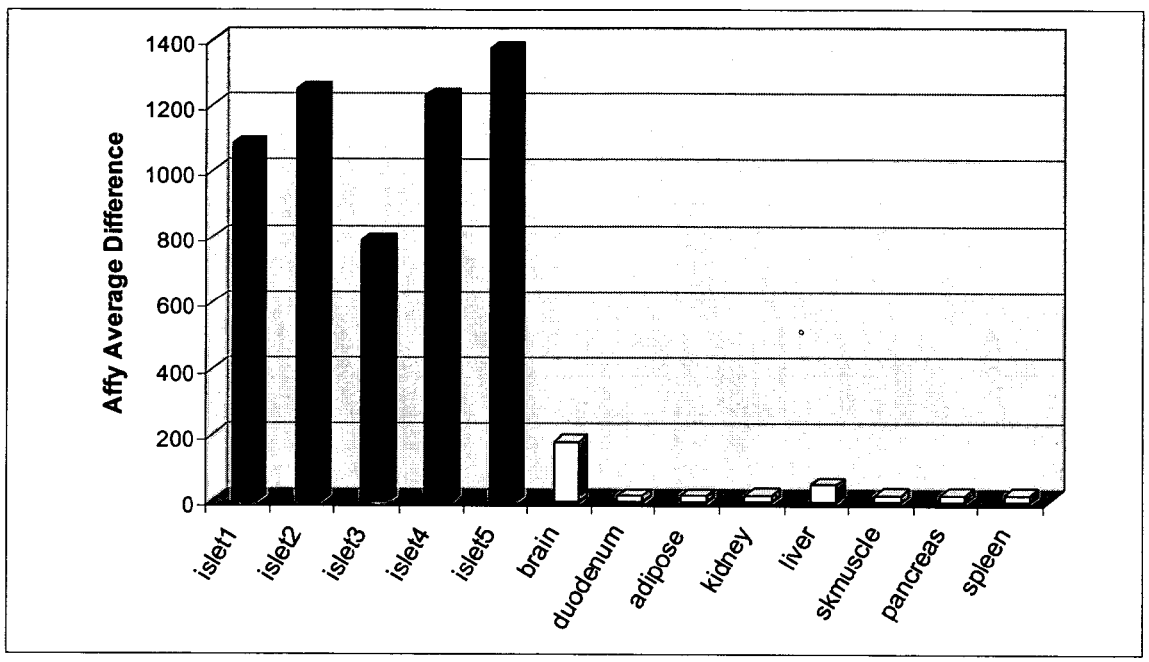
FIG. 5 illustrates rat islet chip hybridization results demonstrating the islet enrichment of BIK mRNA. Chips were hybridized with equivalent amounts of cRNA from five sets of isolated rat islets, as well as the rat tissues: brain, duodenum, adipose, kidney, liver, skeletal muscle, pancreas and spleen. The Average Difference score reflects the relative abundance of the BIK mRNA in each of the tissues. The Affymetrix GeneChip analysis package indicated BIK mRNA was present in all five islet samples and absent in each of the other tissues.
Figure 6:
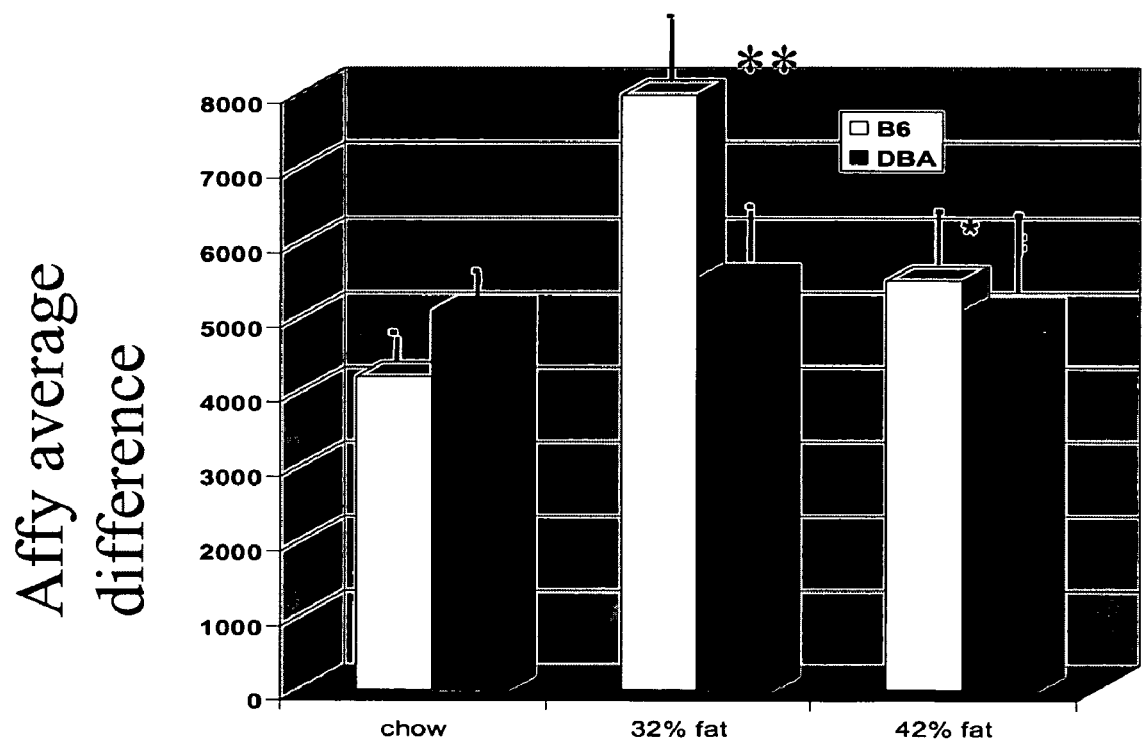
FIG. 6 illustrates mouse islet chip hybridization results demonstrating BIK mRNA is increased by high fat feeding in C57/B6J mice. Mouse strains C57/B6J and DBA were maintained on chow diets, or on 32% or 42% fat diets for 28 weeks. Islets were isolated from 5 or mice from each of the strains under each condition. RNA samples from each were analyzed by mouse islet GeneChips for the content of many thousands of mRNAs. The mRNA for mouse BIK was found to be significantly up-regulated by high fat feeding in C57/B6 animals.

As discussed above, islet enrichment of BIK is apparent in human islets. Mouse islets (FIG. 4), and rat islets (FIG. 5) also demonstrate enrichment for BIK. In addition, expression of BIK mRNA is increased in C57/B6J mice that are fed a high fat diet to mimic the etiology of human Type II diabetes (FIG. 6). The mRNA for this channel is increased almost two-fold in islets from C57/B6J mice that are rendered hyperglycemic by consuming a high fat diet. BIK is also sharply increased in islets of diabetic animals but not in non-diabetic controls. This message is increased 90% (p<0.001) in mice fed a 32% fat diet for 28 weeks relative to chow fed mice at the same time age. There is also a significant, but smaller (30%; p<0.02), increase in BIK mRNA in C57/B6J mice fed at 42% fat diet. No increase was observed in DBA mice fed the same high fat diets relative to chow fed DBA mice. C57B6 islets have defective insulin secretion relative to other strains, and this defect is enhanced by a feeding a high fat diet.

Figure 7:
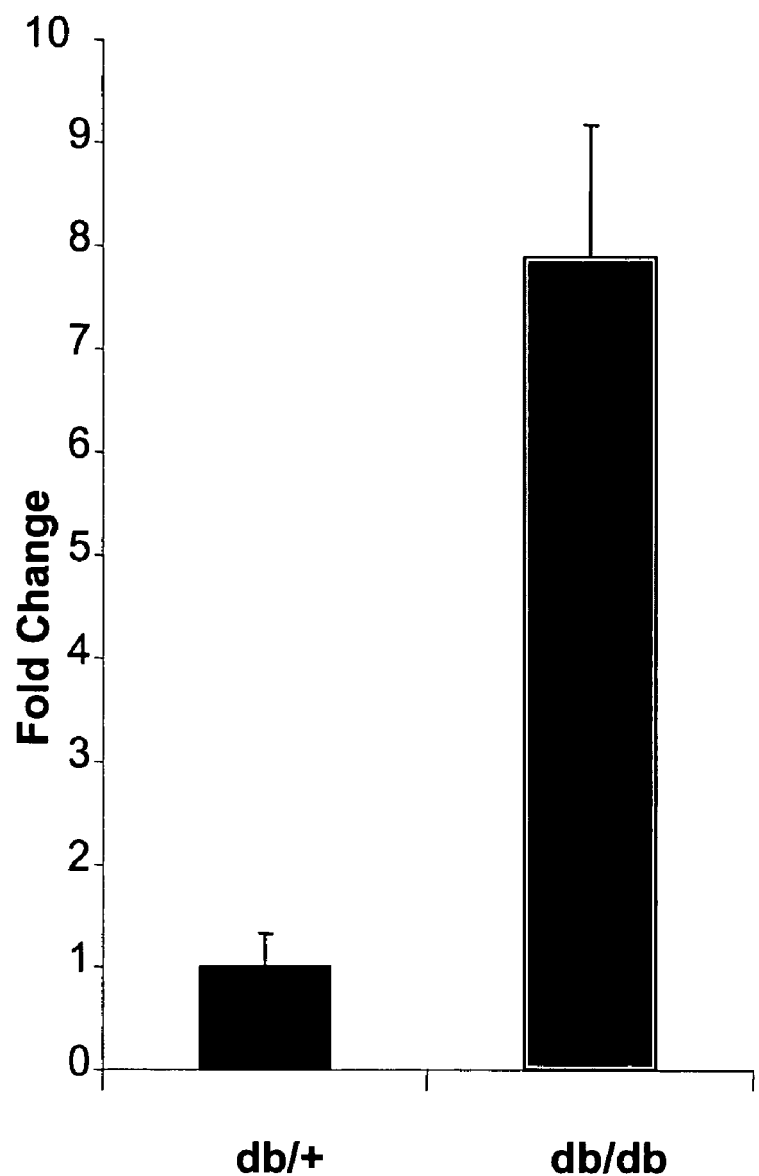
FIG. 7 illustrates mouse islet chip hybridization results demonstrating BIK mRNA is increased in the islets of diabetic (db/db) mice. Islets from diabetic (db/db) and non-diabetic (db/+) mice at 12-weeks of age were isolated and RNA was prepared for analysis by real-time semi-quantitative PCR (TaqMan). The relative fold change for mouse BIK was adjusted for beta-actin mRNA content of the sample.

BIK mRNA is also sharply up-regulated in obese, diabetic (db/db) mice relative to lean, non-diabetic mice (FIG. 7). Given the 'leak' properties of channels comprising two channel-forming domains, BIK may contribute to the insulin secretion defect that is found in these mouse models of Type II diabetes. Without intending to limit the scope of the invention, it is believed that increased expression of the channel is likely to hyperpolarize the cell membrane resulting in decreased insulin secretion, which is characteristic of the islets from these high fat fed mice.

Elevated expression of the islet-specific background/leak $K^+$ channel BIK in diabetic islets suggests that BIK may lead to beta cell membrane hyperpolarization and thereby contribute to the deficit in glucose stimulated insulin secretion (GSIS) that is observed in the islets of diabetic animals. Since beta cell membrane depolarization, primarily mediated via the KATP channel (Kir 6.2+SUR1), is required to activate the voltage dependent L-type Ca++ channels that trigger the release of insulin, hyperpolarization inhibits insulin secretion in response to glucose.

We demonstrated that increasing BIK expression through the use of a recombinant adenovirus renders cells less responsive to glucose stimulated insulin secretion. The mouse beta cell line βHC9 cell normally responds to high (20 mM) glucose with a 3-5 fold increase in insulin release relative to the insulin released in low (0.1 mM) glucose. Infection of βHC9 cells with a control adenovirus that does not contain the BIK coding sequence did not substantially reduce the effect of high glucose on insulin secretion, but infection with a virus causing the expression of human BIK or human BIK tagged with an N-terminal flag epitope each led to a dramatic suppression of glucose stimulated insulin secretion (FIG. 8A). Increasing the expression of BIK or flag-BIK also leads to an increase in cellular content of insulin; this indicates that BIK inhibition of GSIS is not due to the inhibition of insulin biosynthesis (FIG. 8B).

Although βHC9 cells have many of the properties of normal differentiated beta cells within islets, the function of BIK in human insulin secreting beta cells can be directly assessed by BIK adenovirus infection of isolated human islets and subsequent assay of GSIS in these islets. Aliquots of human islets from two different donors were infected with the adenovirus driving BIK expression or a control virus lacking the BIK coding sequence 48 hours prior to analysis of glucose responsiveness by perifusion of the islets with buffers containing low or high glucose or KCl. BIK infected islets were almost completely insensitive to 16 mM glucose. In contrast, control virus infected islets displayed a robust response to this concentration of glucose. Depolarization of the beta cells with KCl does promote insulin release from both BIK infected and control infected islets, but there is less release from the BIK infected islets.

The attenuation of GSIS that results from increasing BIK expression in beta cells or islets suggests that BIK contributes to the negative regulation of insulin release in beta cells via membrane hyperpolarization. In the case of the islets of diabetic db/db mice, BIK likely contributes to the relative glucose insensitivity that is observed in islets from diabetic animals. Small molecule inhibitors of BIK therefore reverses the negative effects of BIK on insulin secretion and restores diabetic islets to a state more like that of normal islets. The resulting improvement in islet function should reverse the insulin deficit that leads to diabetes. BIK inhibitors are therefore excellent candidates for anti-diabetic drugs.

Example 2

Figure 9:
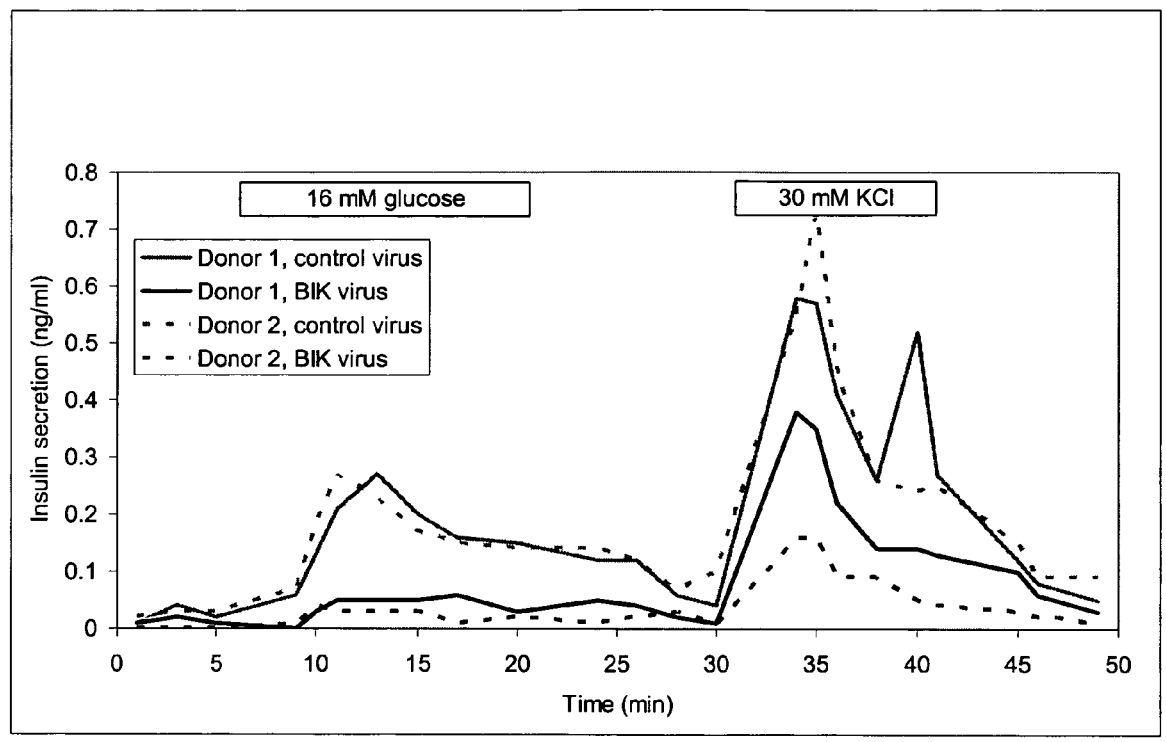
FIG. 9 illustrates the effect of BIK expression on insulin secretion from human islets during perifusion. Cryopreserved human islets from 2 donors were thawed and infected with adenovirus ($5\times10^6$ pfu/50 islets) expressing human BIK or with a control virus that is identical save for lacking the BIK coding sequence. After 48 h the islets were placed in chambers allowing for perifusion of buffers containing low or high glucose or KCl. Insulin secretion was measured from 25 islets of comparable size from each group sequentially exposed to 2 mM glucose for 5 min., 16 mM glucose for 15 min., 2 mM glucose for 10 min., 30 mM KCl for 11 min, and 2 mM glucose for 7 min. Fractions were collected at 1 min. intervals.

This example demonstrates an assay for BIK-dependent membrane hyperpolarization/depolarization and identification of methanandamide as a partially selective inactivator of BIK channels High level expression of a background/leak potassium channel such as BIK in fibroblasts results in hyperpolarization of the plasma membrane. Further, monitoring the membrane potential of these cells provides an assay for detecting small molecule blockers of BIK. We made stable HEK293 cell lines expressing BIK (and the well characterized background channel TASK2 for comparison) and characterized them using a FLIPR Membrane Potential Dye and FlexStation microplate fluorometer. BIK and TASK2 expressing cells displayed substantially decreased basal fluorescence with this dye than stable cell lines containing only the vector or parental HEK293 cells; this decrease is indicative of hyperpolarization. Furthermore, BIK and TASK2 cells display a 3 to 5-fold greater change in fluorescence upon depolarization with 30 mM KCl compared to vector transfected stable cell lines. See, FIG. 9.

Figure 10:
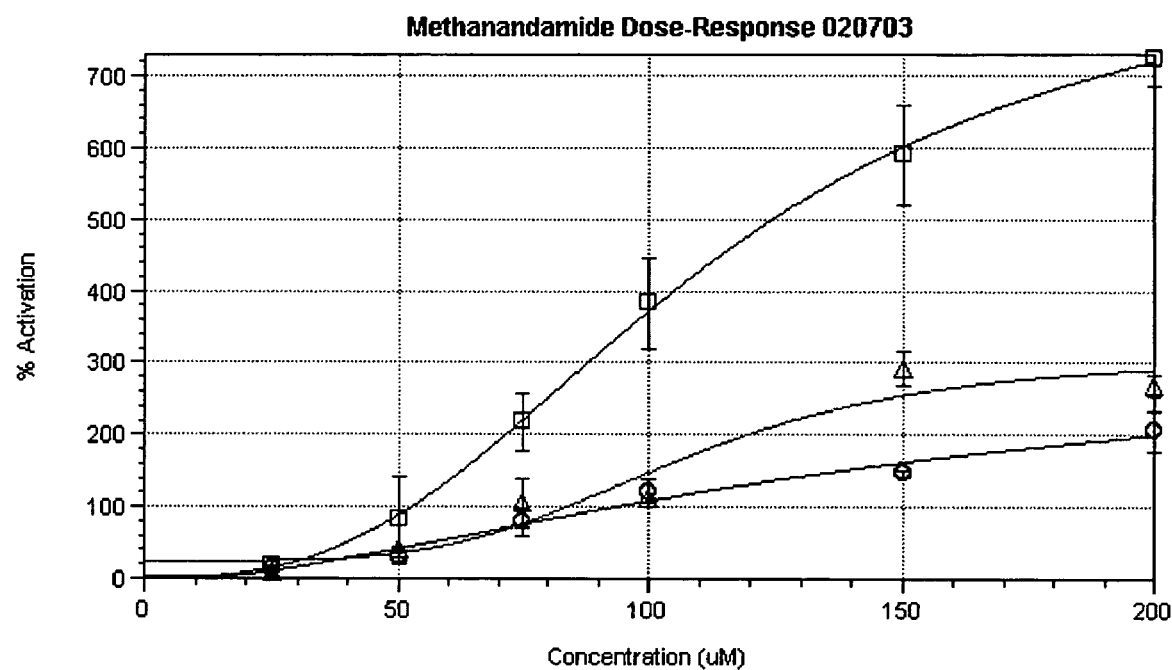
FIG. 10 illustrates that Methanandamide is a partially selective inactivator of BIK. HEK293 cells stably transfected with pcDNA3.1 (circles) or the same vector allowing expression of BIK (squares) or TASK-2 (triangles) were plated in 96 well assay plates 24 h prior to analysis. Cells were incubated in 100 µl of 0.5×FLIPR Membrane Potential Dye (Molecular Devices) for 30 min. Methanandamide dilutions in DMSO were added to the wells by a FlexStation device (Molecular Devices), the fluorescence intensity changes were recorded before, during and after addition of the compound. The fluorescence intensity changes are plotted as the percent increase from the basal value recorded prior to compound addition. The values are the mean and range of duplicate wells. Similar results were obtained in three other independent experiments.

We tested a series of channel blockers and modulators for their ability to selectively block BIK channels in the stable HEK293 transfectants using the FlexStation/Membrane potential dye assay. Methanandamide, the methyl derivative of the endogenous compound anandamide, was found to be a partially selective blocker of BIK in that this compound (at 100 μM) produces a 3 fold greater increase in fluorescence (depolarization) in BIK cells than in TASK2 or vector control cells (FIG. 10A).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated polynucleotide encoding a potassium channel polypeptide, wherein the polypeptide comprises the sequence of SEQ ID NO: 10, with the proviso that the polypeptide is not SEQ ID NO: 9.

2. The polynucleotide of claim 1, wherein the potassium channel polypeptide comprises SEQ ID NO:2.

3. The isolated polynucleotide of claim 1, wherein the potassium channel polypeptide comprises SEQ ID NO:1.

4. A cell comprising a recombinant expression cassette, the expression cassette comprising a promoter operably linked to a polynucleotide encoding a potassium channel polypeptide comprising the sequence of SEQ ID NO: 10, with the proviso that the polypeptide is not SEQ ID NO: 9.

5. The cell of claim 4, wherein the polypeptide comprises SEQ ID NO:2.

* * * * *

SEQUENCE LISTING

```
<160> NUMBER OF SEQ ID NOS: 24

<210> SEQ ID NO 1
<211> LENGTH: 2036
<212> TYPE: DNA
<213> ORGANISM: Homo sapiens
<220> FEATURE:
<223> OTHER INFORMATION: human beta-cell inhibitory potassium channel,
      islet cell two-pore acid-sensitive K channel (BIK)
      cDNA

<400> SEQUENCE: 1
caggcggcag cctgggcaca ggccsctagg tgcttactcc tcacctgttt cccacctctc      60
ccccatagcc agcccacgg ccctggcagg gtcctggcca cagcatgccc agtgctgggc     120
tctgcagctg ctggggtggc cgggtgctgc ccctgctgct ggcctatgtc tgctacctgc     180
tgctcggtgc cactatcttc cagctgctag agaggcaggc ggaggctcag tccagggacc     240
```

-continued

```
agtttcagtt ggagaagctg cgcttcctgg agaactacac ctgcctggac cagtgggcca    300
tggagcagtt tgtgcaggtc atcatggaag cctgggtgaa aggtgtgaac cccaaaggca    360
actctaccaa ccccagcaac tgggactttg cagcagttt cttctttgca ggcacagtcg    420
tcactaccat aggatatggg aacctggcac ccagcacaga ggcaggtcag gtcttctgtg    480
tcttctatgc cctgttgggc atcccgctta acgtgatctt cctcaaccac ctgggcacag    540
ggctgcgtgc ccatctggcc gccattgaaa gatgggagga ccgtcccagg cgctcccagg    600
tactgcaagt cctgggcctg gctctgttcc tgaccctggg gacgctggtc attctcatct    660
tcccacccat ggtcttcagc catgtggagg ctggagctt cagcgagggc ttctactttg    720
ctttcatcac tctcagcacc attggctttg gggactatgt tgttggcaca gaccccagca    780
agcattatat ctcagtgtac cggagcctgg cagccatctg gatcctcctg ggcctggcgt    840
ggctggcgct gatcctccca ctgggcccc tgcttctgca cagatgctgc cagctctggc    900
tgctcagtag gggcctcggc gtcaaggatg gggaagcctc tgaccccagt gggctcccca    960
ggcctcagaa gatccccatc tctgcatgag gccccgggg gggcccaga aaccccttc     1020
atcctcccca gtcccaccct atctgctctc tggatttcca gccctgcttt ctcctctccc    1080
aaccccctca cttctcagcc agggctggtc tcaggagctc tcccaagaga gaaaggagac    1140
aggtatatcc aagaaagtaa cagagaggag acgtgagata ggattaaaga tatgtgtgga    1200
tggggaggtg taccccttgtc ccagagcccc tgccacagcc ttccacccaa aggtagtggc    1260
cagatctcca ctgcccctccc catgcccct tccaggagac cttacacaaa caaggatga    1320
ctttacttt gcctcatttg atatgtgcac agtgcattg ccaagcccct actatgtgcc    1380
aggtgctgtg ccagggtctg tgccagggtc tggggataca gcagtggaag tgcctgccct    1440
tgatgtgcct ttagttgcta ggcaagcaaa gaggcagccc caacacagtg cccaaaatgc    1500
tatgatggga atagccccag ggttgatgag agcccatggg aatggctggc agggagcatc    1560
aaagagaggg gagacctggg cagagacttt ggaacaatct tagtgaaaag aggatctctg    1620
ccctcaggaa gctctcagcc gaggggcagg cgagctgcct ctcaaagctc gccagctccc    1680
cttgcctaga agtccagggc tgtctgtgaa caaagcttag gacctcttgg gtgtcctacc    1740
cactttcctg aacatggcct tctcagaagc aaggagtgga caagcctctt ggttaaggct    1800
cctcttacct cccaagctca tggacaagtg gcaatcagct ggggtccctc ttttgggta    1860
caaaggaaag gacagaggtg tgggagaccc aaggtggtct tgagattgac agacagcaag    1920
tccttggaga tagcccccga gtccaagaac ttaggcaggg gccccaagac aataaagttg    1980
gtctctacta tctcctaaaa aaaaaaaaaa aaaaaaaaa aaaaaaaaaa aaaacc          2036
```

<210> SEQ ID NO 2
<211> LENGTH: 294
<212> TYPE: PRT
<213> ORGANISM: Homo sapiens
<220> FEATURE:
<223> OTHER INFORMATION: human beta-cell inhibitory potassium channel,
      islet cell two-pore acid-sensitive K channel (BIK)

<400> SEQUENCE: 2

Met Pro Ser Ala Gly Leu Cys Ser Cys Trp Gly Gly Arg Val Leu Pro
1               5                   10                  15

Leu Leu Leu Ala Tyr Val Cys Tyr Leu Leu Leu Gly Ala Thr Ile Phe
            20                  25                  30

Gln Leu Leu Glu Arg Gln Ala Glu Ala Gln Ser Arg Asp Gln Phe Gln

```
                35                  40                  45
Leu Glu Lys Leu Arg Phe Leu Glu Asn Tyr Thr Cys Leu Asp Gln Trp
     50                  55                  60

Ala Met Glu Gln Phe Val Gln Val Ile Met Glu Ala Trp Val Lys Gly
 65                  70                  75                  80

Val Asn Pro Lys Gly Asn Ser Thr Asn Pro Ser Asn Trp Asp Phe Gly
                 85                  90                  95

Ser Ser Phe Phe Phe Ala Gly Thr Val Val Thr Ile Gly Tyr Gly
                100                 105                 110

Asn Leu Ala Pro Ser Thr Glu Ala Gly Gln Val Phe Cys Val Phe Tyr
                115                 120                 125

Ala Leu Leu Gly Ile Pro Leu Asn Val Ile Phe Leu Asn His Leu Gly
            130                 135                 140

Thr Gly Leu Arg Ala His Leu Ala Ala Ile Glu Arg Trp Glu Asp Arg
145                 150                 155                 160

Pro Arg Arg Ser Gln Val Leu Gln Val Leu Gly Leu Ala Leu Phe Leu
                165                 170                 175

Thr Leu Gly Thr Leu Val Ile Leu Ile Phe Pro Pro Met Val Phe Ser
                180                 185                 190

His Val Glu Gly Trp Ser Phe Ser Glu Gly Phe Tyr Phe Ala Phe Ile
            195                 200                 205

Thr Leu Ser Thr Ile Gly Phe Gly Asp Tyr Val Val Gly Thr Asp Pro
210                 215                 220

Ser Lys His Tyr Ile Ser Val Tyr Arg Ser Leu Ala Ala Ile Trp Ile
225                 230                 235                 240

Leu Leu Gly Leu Ala Trp Leu Ala Leu Ile Leu Pro Leu Gly Pro Leu
                245                 250                 255

Leu Leu His Arg Cys Cys Gln Leu Trp Leu Leu Ser Arg Gly Leu Gly
            260                 265                 270

Val Lys Asp Gly Glu Ala Ser Asp Pro Ser Gly Leu Pro Arg Pro Gln
            275                 280                 285

Lys Ile Pro Ile Ser Ala
    290
```

<210> SEQ ID NO 3
<211> LENGTH: 2351
<212> TYPE: DNA
<213> ORGANISM: Rattus sp.
<220> FEATURE:
<223> OTHER INFORMATION: rat beta-cell inhibitory potassium channel,
      islet cell two-pore acid-sensitive K channel (BIK) cDNA
<220> FEATURE:
<221> NAME/KEY: modified_base
<222> LOCATION: (1)..(2351)
<223> OTHER INFORMATION: n = g, a, c or t

<400> SEQUENCE: 3

```
catcatgccc cgtgctgggg tctgcagctg ctggggtggc caagtattgc ccctacttct      60
ggcctatatc tgctacctgc tgcttggggc caccatcttc cagcggctgg agaagcaggc     120
agaggctcag tccagggacc agttccagct ggaaaaactg cgcttcttag agaactacac     180
ctgcctggac cagcaggccc tggagcagtt cgtacaggtc atcctggaag cctgggtgaa     240
aggtgtgaac cccaaaggca actccaccaa ccccagcaac tgggacttcg ggagcagttt     300
cttctttgca ggcacagtgg tcactaccat aggttatgga aacctggcac ccagcacgga     360
ggcagggcag gtcttctgtg tcttctatgc cctgatggga atcccactca acgtggtctt     420
```

```
tctcaaccat ctgggcacag ggctgcgtgc ccatctgacc acactggaca ggtgggagga      480
ccaccccagg cattcccagc tcctgcaggt cctgggcctg gctctgttcc tgaccttggg      540
gaccctggtc attctcatct tcccgcccat gttcttcagc cacgtggagg ctggagctt       600 ccgtgagggc ttctacttcg ccttcatcac cctcagcacc attggcttcg gggactatgt      660
tgtcggcaca gacccagca agcactacat tgcggtgtat cggagcttgg cagctatatg       720
gatcctcctg ggcctggcgt ggctggcagt ggtcctcagc ttgggatccc tgcttctgca      780
caggtgctcc cggctctggc agcttatccg aggcctggac gttaaggacg gagcagcccc      840
gggctctgag cccagatcac agaaaatccc cttctctgca tgagaccag gtgtcctgac       900 ctgccctccc caaacccgtg acattccctg cccttccctt aaccctaacc tcccccacc      960 ccccccctgc ccacactacc cagcaactct ccagggagaa aaggagaca gatgaaccta      1020 cagagtaact gaggggagac aaggagacaa aatcaaagtc tgtgtgggtg gagatgtcaa      1080
ggttgccctg tttcccaaag agaacctgga ggagaagtta aacccgacat gaatcgtggc      1140
cgagtcacta ttgccatctt aatgtagtaa cgggacccct taggctgcaa gcaaaagcgg      1200
acttgattgt tgtatcattt acgatctaca tggcaggctc ttaacaggtc cgtactaggt      1260
agcaggcgct gtgcctggtt ctagggcttt gacagtggtg gtctgggctg tgctgtgtcg      1320
tcagtcttga aggagccccc gaggcagcgt cctcatcttt gatgggaata acctggggga     1380
gaatgaaagt tcagggcagt ggctggagga ggagagctgg acacacacct ggggacacct      1440
ttggtgtccc caagaagcca tcctcaggag tctcacagct gaggaacaag aagcctgccg      1500
gtcagttctc cagctctcct tgcttacaag tggagaggga tcctagaaca cacggggga     1560 ccccttcag gtgtcccacc actttcctga acatgacctc ccctgaccct cagagcactc       1620
ttagacctct ttactccccc tgagaagctg ggggcagggt gggggcagca gatcccaaga      1680
gcttcataga ctgtgccctc cttaatggta tggactcccc tgggaacact cttcatctga      1740
gcctggtcct tctgccagac tgcgacactg gccagaagg gagagacggt ttggcccaga       1800
ctcacgggat tgggaaytaa ttttgtgktt ngacttcctt cccttctcca gtgacagagg      1860
ggttcccaaa ttctgtgtct tctttatagc attaagggtg gggtgngact gtgagcccca      1920
gaggttgagg ggagtcccag ggaaggaccc acattggcag agggttccca gcacccaagt      1980
cttactgcca cccagggaaa gattcaactc ggatgtctcc aacacgtcta cacacgctgg      2040
accccgcttc tgttctgggt gcatggagat gcagggactt ccctccaaag cagccaggaa      2100
agttcgctct cgttctcttg cctgctaacc tcccaacccg cggtcagcac agacaaacca      2160 tgccacctg gccccctattt tatttatttt agtaaactgg ctgtagggag atctaggatg      2220
acgcaagcat gcatttggaa gacgtccgtg gcccctcagc ttaggcagga gtccggtgtt      2280
aataaacttg gctgctgttt cttcaaaaaa aaaaaaaaaa aaaaaaaaaa aaaaaaaaaa      2340
aaaaaaaaaa a                                                            2351
```

<210> SEQ ID NO 4
<211> LENGTH: 292
<212> TYPE: PRT
<213> ORGANISM: Rattus sp.
<220> FEATURE:
<223> OTHER INFORMATION: rat beta-cell inhibitory potassium channel,
      islet cell two-pore acid-sensitive K channel (BIK)

<400> SEQUENCE: 4

Met Pro Arg Ala Gly Val Cys Ser Cys Trp Gly Gly Gln Val Leu Pro
1               5                   10                  15

```
Leu Leu Leu Ala Tyr Ile Cys Tyr Leu Leu Gly Ala Thr Ile Phe
             20                  25                  30

Gln Arg Leu Glu Lys Gln Ala Glu Ala Gln Ser Arg Asp Gln Phe Gln
         35                  40                  45

Leu Glu Lys Leu Arg Phe Leu Glu Asn Tyr Thr Cys Leu Asp Gln Gln
     50                  55                  60

Ala Leu Glu Gln Phe Val Gln Val Ile Leu Glu Ala Trp Val Lys Gly
 65                  70                  75                  80

Val Asn Pro Lys Gly Asn Ser Thr Asn Pro Ser Asn Trp Asp Phe Gly
                 85                  90                  95

Ser Ser Phe Phe Phe Ala Gly Thr Val Val Thr Thr Ile Gly Tyr Gly
            100                 105                 110

Asn Leu Ala Pro Ser Thr Glu Ala Gly Gln Val Phe Cys Val Phe Tyr
        115                 120                 125

Ala Leu Met Gly Ile Pro Leu Asn Val Val Phe Leu Asn His Leu Gly
130                 135                 140

Thr Gly Leu Arg Ala His Leu Thr Thr Leu Asp Arg Trp Glu Asp His
145                 150                 155                 160

Pro Arg His Ser Gln Leu Leu Gln Val Leu Gly Leu Ala Leu Phe Leu
                165                 170                 175

Thr Leu Gly Thr Leu Val Ile Leu Ile Phe Pro Pro Met Phe Phe Ser
            180                 185                 190

His Val Glu Gly Trp Ser Phe Arg Glu Gly Phe Tyr Phe Ala Phe Ile
        195                 200                 205

Thr Leu Ser Thr Ile Gly Phe Gly Asp Tyr Val Val Gly Thr Asp Pro
    210                 215                 220

Ser Lys His Tyr Ile Ala Val Tyr Arg Ser Leu Ala Ala Ile Trp Ile
225                 230                 235                 240

Leu Leu Gly Leu Ala Trp Leu Ala Val Val Leu Ser Leu Gly Ser Leu
                245                 250                 255

Leu Leu His Arg Cys Ser Arg Leu Trp Gln Leu Ile Arg Gly Leu Asp
            260                 265                 270

Val Lys Asp Gly Ala Ala Pro Gly Ser Glu Pro Arg Ser Gln Lys Ile
        275                 280                 285

Pro Phe Ser Ala
        290

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:Primer 1,
      forward primer includes start codon of hBIK

<400> SEQUENCE: 5
agaggtcgac atgcccagtg ctgggctct                                        29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:Primer 2,
      reverse primer includes stop codon of hBIK

<400> SEQUENCE: 6
```

```
agagaagctt tcatgcagag atggggat                                      28
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Primer 3, internal forward primer in human coding region

<400> SEQUENCE: 7

```
aagtcctggg cctggctct                                                19
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:Primer 4, internal reverse primer in human coding region

<400> SEQUENCE: 8

```
agagccaggc ccaggactt                                                19
```

<210> SEQ ID NO 9
<211> LENGTH: 294
<212> TYPE: PRT
<213> ORGANISM: Homo sapiens
<220> FEATURE:
<223> OTHER INFORMATION: BIK potassium channel variant allele, GenBank Accession #CAC07336

<400> SEQUENCE: 9

```
Met Pro Ser Ala Gly Leu Cys Ser Cys Trp Gly Gly Arg Val Leu Pro
 1               5                  10                  15

Leu Leu Leu Ala Tyr Val Cys Tyr Leu Leu Leu Gly Ala Thr Ile Phe
             20                  25                  30

Gln Leu Leu Glu Arg Gln Ala Glu Ala Gln Ser Arg Asp Gln Phe Gln
         35                  40                  45

Leu Glu Lys Leu Arg Phe Leu Glu Asn Tyr Thr Cys Leu Asp Gln Trp
     50                  55                  60

Ala Met Glu Gln Phe Val Gln Val Ile Met Glu Ala Trp Val Lys Gly
 65                  70                  75                  80

Val Asn Pro Lys Gly Asn Ser Thr Asn Pro Ser Asn Trp Asp Phe Gly
                 85                  90                  95

Ser Ser Phe Phe Phe Ala Gly Thr Val Val Thr Thr Ile Gly Tyr Gly
            100                 105                 110

Asn Leu Ala Pro Ser Thr Glu Ala Gly Gln Val Phe Cys Val Phe Tyr
        115                 120                 125

Ala Leu Leu Gly Ile Pro Leu Asn Val Ile Phe Leu Asn His Leu Gly
    130                 135                 140

Thr Gly Leu Arg Ala His Leu Ala Ala Ile Glu Arg Trp Glu Asp Arg
145                 150                 155                 160

Pro Arg Arg Ser Gln Val Leu Gln Val Leu Gly Leu Ala Leu Phe Leu
                165                 170                 175

Thr Leu Gly Thr Leu Val Ile Leu Ile Phe Pro Pro Met Val Phe Ser
            180                 185                 190

His Val Glu Gly Trp Ser Phe Ser Glu Gly Phe Tyr Phe Ala Phe Ile
        195                 200                 205

Thr Leu Ser Thr Ile Gly Phe Gly Asp Tyr Val Val Gly Thr Asp Pro
```

```
            210                 215                 220
Ser Lys His Tyr Ile Ser Val Tyr Arg Ser Leu Ala Ala Ile Trp Ile
225                 230                 235                 240

Leu Leu Gly Leu Ala Trp Leu Ala Leu Ile Leu Pro Leu Gly Pro Leu
                245                 250                 255

Leu Leu His Arg Cys Cys Gln Leu Trp Leu Leu Ser Arg Gly Leu Gly
                260                 265                 270

Val Lys Asp Gly Ala Ala Ser Asp Pro Ser Gly Leu Pro Arg Pro Gln
            275                 280                 285

Lys Ile Pro Ile Ser Ala
            290

<210> SEQ ID NO 10
<211> LENGTH: 294
<212> TYPE: PRT
<213> ORGANISM: Artificial Sequence
<220> FEATURE:
<223> OTHER INFORMATION: Description of Artificial Sequence:consensus
      sequence between human and rat BIK
<220> FEATURE:
<221> NAME/KEY: MOD_RES
<222> LOCATION: (1)..(294)
<223> OTHER INFORMATION: Xaa = any amino acid

<400> SEQUENCE: 10

Met Pro Xaa Ala Gly Xaa Cys Ser Cys Trp Gly Gly Xaa Val Leu Pro
  1               5                  10                  15

Leu Leu Leu Ala Tyr Xaa Cys Tyr Leu Leu Gly Ala Thr Ile Phe
                 20                  25                  30

Gln Xaa Leu Glu Xaa Gln Ala Glu Ala Gln Ser Arg Asp Gln Phe Gln
             35                  40                  45

Leu Glu Lys Leu Arg Phe Leu Glu Asn Tyr Thr Cys Leu Asp Gln Xaa
 50                  55                  60

Ala Xaa Glu Gln Phe Val Gln Val Ile Xaa Glu Ala Trp Val Lys Gly
 65                  70                  75                  80

Val Asn Pro Lys Gly Asn Ser Thr Asn Pro Ser Asn Trp Asp Phe Gly
                 85                  90                  95

Ser Ser Phe Phe Phe Ala Gly Thr Val Val Thr Thr Ile Gly Tyr Gly
                100                 105                 110

Asn Leu Ala Pro Ser Thr Glu Ala Gly Gln Val Phe Cys Val Phe Tyr
                115                 120                 125

Ala Leu Xaa Gly Ile Pro Leu Asn Val Xaa Phe Leu Asn His Leu Gly
            130                 135                 140

Thr Gly Leu Arg Ala His Leu Xaa Xaa Xaa Xaa Arg Trp Glu Asp Xaa
145                 150                 155                 160

Pro Arg Xaa Ser Gln Xaa Leu Gln Val Leu Gly Leu Ala Leu Phe Leu
                165                 170                 175

Thr Leu Gly Thr Leu Val Ile Leu Ile Phe Pro Pro Met Xaa Phe Ser
                180                 185                 190

His Val Glu Gly Trp Ser Phe Xaa Glu Gly Phe Tyr Phe Ala Phe Ile
                195                 200                 205

Thr Leu Ser Thr Ile Gly Phe Gly Asp Tyr Val Val Gly Thr Asp Pro
            210                 215                 220

Ser Lys His Tyr Ile Xaa Val Tyr Arg Ser Leu Ala Ala Ile Trp Ile
225                 230                 235                 240

Leu Leu Gly Leu Ala Trp Leu Ala Xaa Xaa Leu Xaa Leu Gly Xaa Leu
                245                 250                 255
```

```
Leu Leu His Arg Cys Xaa Xaa Leu Trp Xaa Leu Xaa Arg Gly Leu Xaa
                260                 265                 270

Val Lys Asp Gly Xaa Xaa Xaa Pro Xaa Xaa Xaa Pro Arg Xaa Gln
        275                 280                 285

Lys Ile Pro Xaa Ser Ala
    290

<210> SEQ ID NO 11
<211> LENGTH: 239
<212> TYPE: PRT
<213> ORGANISM: Homo sapiens
<220> FEATURE:
<223> OTHER INFORMATION: transmembrane (TM) and pore domains of human
      beta-cell inhibitory potassium channel, islet cell
      two-pore acid-sensitive K channel (BIK)

<400> SEQUENCE: 11

Arg Val Leu Pro Leu Leu Ala Tyr Val Cys Tyr Leu Leu Gly
  1               5                  10                  15

Ala Thr Ile Phe Gln Leu Leu Glu Arg Gln Ala Glu Ala Gln Ser Arg
             20                  25                  30

Asp Gln Phe Gln Leu Glu Lys Leu Arg Phe Leu Glu Asn Tyr Thr Cys
         35                  40                  45

Leu Asp Gln Trp Ala Met Glu Gln Phe Val Gln Val Ile Met Glu Ala
     50                  55                  60

Trp Val Lys Gly Val Asn Pro Lys Gly Asn Ser Thr Asn Pro Ser Asn
 65                  70                  75                  80

Trp Asp Phe Gly Ser Ser Phe Phe Ala Gly Thr Val Val Thr Thr
                 85                  90                  95

Ile Gly Tyr Gly Asn Leu Ala Pro Ser Thr Glu Ala Gly Gln Val Phe
                100                 105                 110

Cys Val Phe Tyr Ala Leu Leu Gly Ile Pro Leu Asn Val Ile Phe Leu
            115                 120                 125

Asn His Leu Gly Thr Gly Leu Arg Ala His Leu Ala Ala Ile Glu Arg
        130                 135                 140

Trp Glu Asp Arg Pro Arg Arg Ser Gln Val Leu Gln Val Leu Gly Leu
145                 150                 155                 160

Ala Leu Phe Leu Thr Leu Gly Thr Leu Val Ile Leu Ile Phe Pro Pro
                165                 170                 175

Met Val Phe Ser His Val Glu Gly Trp Ser Phe Ser Glu Gly Phe Tyr
            180                 185                 190

Phe Ala Phe Ile Thr Leu Ser Thr Ile Gly Phe Gly Asp Tyr Val Val
        195                 200                 205

Gly Thr Asp Pro Ser Lys His Tyr Ile Ser Val Tyr Arg Ser Leu Ala
    210                 215                 220

Ala Ile Trp Ile Leu Leu Gly Leu Ala Trp Leu Ala Leu Ile Leu
225                 230                 235

<210> SEQ ID NO 12
<211> LENGTH: 258
<212> TYPE: PRT
<213> ORGANISM: Homo sapiens
<220> FEATURE:
<223> OTHER INFORMATION: transmembrane (TM) and pore domains of human
      tandem pore domain potassium channel THIK-1

<400> SEQUENCE: 12

Arg Phe Leu Leu Leu Ala Ala Leu Ile Val Leu Tyr Leu Leu Gly Gly
```

```
                1               5              10              15
Ala Ala Val Phe Ser Ala Leu Glu Leu Ala His Glu Arg Gln Ala Lys
                   20                   25                   30

Gln Arg Trp Glu Glu Arg Leu Ala Asn Phe Ser Arg Gly His Asn Leu
               35                   40                   45

Ser Arg Asp Glu Leu Arg Gly Phe Leu Arg His Tyr Glu Glu Ala Thr
           50                   55                   60

Arg Ala Gly Ile Arg Val Asp Asn Val Arg Pro Arg Trp Asp Phe Thr
 65                  70                   75                   80

Gly Ala Phe Tyr Phe Val Gly Thr Val Ser Thr Ile Gly Phe Gly
                   85                   90                   95

Met Thr Thr Pro Ala Thr Val Gly Gly Lys Ile Phe Leu Ile Phe Tyr
                  100                  105                  110

Gly Leu Val Gly Cys Ser Ser Thr Ile Leu Phe Phe Asn Leu Phe Leu
                  115                  120                  125

Glu Arg Leu Ile Thr Ile Ile Ala Tyr Ile Met Lys Ser Cys His Gln
                  130                  135                  140

Arg Gln Leu Arg Arg Arg Gly Ala Leu Pro Gln Glu Ser Leu Lys Asp
145                  150                  155                  160

Ala Gly Gln Cys Glu Val Asp Ser Leu Ala Gly Trp Lys Pro Ser Val
                  165                  170                  175

Tyr Tyr Val Met Leu Ile Leu Cys Thr Ala Ser Ile Leu Ile Ser Cys
                  180                  185                  190

Cys Ala Ser Ala Met Tyr Thr Pro Ile Glu Gly Trp Ser Tyr Phe Asp
                  195                  200                  205

Ser Leu Tyr Phe Cys Phe Val Ala Phe Ser Thr Ile Gly Phe Gly Asp
        210                  215                  220

Leu Val Ser Ser Gln Asn Ala His Tyr Glu Ser Gln Gly Leu Tyr Arg
225                  230                  235                  240

Phe Ala Asn Phe Val Phe Ile Leu Met Gly Val Cys Cys Ile Tyr Ser
                  245                  250                  255

Leu Phe

<210> SEQ ID NO 13
<211> LENGTH: 239
<212> TYPE: PRT
<213> ORGANISM: Homo sapiens
<220> FEATURE:
<223> OTHER INFORMATION: transmembrane (TM) and pore domains of human
      TWIK-related acid-sensitive potassium channel 2
      (TASK-2)

<400> SEQUENCE: 13

Arg Gly Pro Leu Leu Thr Ser Ala Ile Ile Phe Tyr Leu Ala Ile Gly
 1               5                  10                  15

Ala Ala Ile Phe Glu Val Leu Glu Glu Pro His Trp Lys Glu Ala Lys
                   20                   25                   30

Lys Asn Tyr Tyr Thr Gln Lys Leu His Leu Leu Lys Glu Phe Pro Cys
               35                   40                   45

Leu Gly Gln Glu Gly Leu Asp Lys Ile Leu Glu Val Val Ser Asp Ala
           50                   55                   60

Ala Gly Gln Gly Val Ala Ile Thr Gly Asn Gln Thr Phe Asn Asn Trp
 65                  70                   75                   80

Asn Trp Pro Asn Ala Met Ile Phe Ala Ala Thr Val Ile Thr Thr Ile
                   85                   90                   95
```

```
Gly Tyr Gly Asn Val Ala Pro Lys Thr Pro Ala Gly Arg Leu Phe Cys
             100                 105                 110

Val Phe Tyr Gly Leu Phe Gly Val Pro Leu Cys Leu Thr Trp Ile Ser
             115                 120                 125

Ala Leu Gly Lys Phe Phe Gly Gly Arg Ala Lys Arg Leu Gly Gln Phe
             130                 135                 140

Leu Thr Lys Arg Gly Val Ser Leu Arg Lys Ala Gln Ile Thr Cys Thr
145                 150                 155                 160

Val Ile Phe Ile Val Trp Gly Val Leu Val His Leu Val Ile Pro Pro
                 165                 170                 175

Phe Val Phe Met Val Thr Glu Gly Trp Asn Tyr Ile Glu Gly Leu Tyr
                 180                 185                 190

Tyr Ser Phe Ile Thr Ile Ser Thr Ile Gly Phe Gly Asp Phe Val Ala
                 195                 200                 205

Gly Val Asn Pro Ser Ala Asn Tyr His Ala Leu Tyr Arg Tyr Phe Val
             210                 215                 220

Glu Leu Trp Ile Tyr Leu Gly Leu Ala Trp Leu Ser Leu Phe Val
225                 230                 235

<210> SEQ ID NO 14
<211> LENGTH: 241
<212> TYPE: PRT
<213> ORGANISM: Homo sapiens
<220> FEATURE:
<223> OTHER INFORMATION: transmembrane (TM) and pore domains of human
      potassium channel TWIK-1

<400> SEQUENCE: 14

Gly Phe Leu Val Leu Gly Tyr Leu Leu Tyr Leu Val Phe Gly Ala Val
1               5                   10                  15

Val Phe Ser Ser Val Glu Leu Pro Tyr Glu Asp Leu Leu Arg Gln Glu
             20                  25                  30

Leu Arg Lys Leu Lys Arg Arg Phe Leu Glu Glu His Glu Cys Leu Ser
             35                  40                  45

Glu Gln Gln Leu Glu Gln Phe Leu Gly Arg Val Leu Glu Ala Ser Asn
         50                  55                  60

Tyr Gly Val Ser Val Leu Ser Asn Ala Ser Gly Asn Trp Asn Trp Asp
65                  70                  75                  80

Phe Thr Ser Ala Leu Phe Phe Ala Ser Thr Val Leu Ser Thr Thr Gly
                 85                  90                  95

Tyr Gly His Thr Val Pro Leu Ser Asp Gly Gly Lys Ala Phe Cys Ile
             100                 105                 110

Ile Tyr Ser Val Ile Gly Ile Pro Phe Thr Leu Leu Phe Leu Thr Ala
             115                 120                 125

Val Val Gln Arg Ile Thr Val His Val Thr Arg Arg Pro Val Leu Tyr
             130                 135                 140

Phe His Ile Arg Trp Gly Phe Ser Lys Gln Val Val Ala Ile Val His
145                 150                 155                 160

Ala Val Leu Leu Gly Phe Val Thr Val Ser Cys Phe Phe Phe Ile Pro
                 165                 170                 175

Ala Ala Val Phe Ser Val Leu Glu Asp Asp Trp Asn Phe Leu Glu Ser
                 180                 185                 190

Phe Tyr Phe Cys Phe Ile Ser Leu Ser Thr Ile Gly Leu Gly Asp Tyr
             195                 200                 205

Val Pro Gly Glu Gly Tyr Asn Gln Lys Phe Arg Glu Leu Tyr Lys Ile
```

```
               210                 215                 220
Gly Ile Thr Cys Tyr Leu Leu Gly Leu Ile Ala Met Leu Val Val
225                 230                 235                 240

Leu

<210> SEQ ID NO 15
<211> LENGTH: 233
<212> TYPE: PRT
<213> ORGANISM: Mus sp.
<220> FEATURE:
<223> OTHER INFORMATION: transmembrane (TM) and pore domains of mouse
      TWIK-related acid-sensitive potassium channel 1
      (TASK-1)

<400> SEQUENCE: 15

Arg Thr Leu Ala Leu Ile Val Cys Thr Phe Thr Tyr Leu Leu Val Gly
  1               5                  10                  15

Ala Ala Val Phe Asp Ala Leu Glu Ser Glu Pro Glu Met Ile Glu Arg
             20                  25                  30

Gln Arg Leu Glu Leu Arg Gln Leu Glu Leu Arg Ala Arg Tyr Asn Leu
         35                  40                  45

Ser Glu Gly Gly Tyr Glu Glu Leu Glu Arg Val Val Leu Arg Leu Lys
     50                  55                  60

Pro His Lys Ala Gly Val Gln Trp Arg Phe Ala Gly Ser Phe Tyr Phe
 65                  70                  75                  80

Ala Ile Thr Val Ile Thr Thr Ile Gly Tyr Gly His Ala Ala Pro Ser
                 85                  90                  95

Thr Asp Gly Gly Lys Val Phe Cys Met Phe Tyr Ala Leu Leu Gly Ile
            100                 105                 110

Pro Leu Thr Leu Val Met Phe Gln Ser Leu Gly Glu Arg Ile Asn Thr
        115                 120                 125

Phe Val Arg Tyr Leu Leu His Arg Ala Lys Arg Gly Leu Gly Met Arg
    130                 135                 140

His Ala Glu Val Ser Met Ala Asn Met Val Leu Ile Gly Phe Val Ser
145                 150                 155                 160

Cys Ile Ser Thr Leu Cys Ile Gly Ala Ala Ala Phe Ser Tyr Tyr Glu
                165                 170                 175

Arg Trp Thr Phe Phe Gln Ala Tyr Tyr Tyr Cys Phe Ile Thr Leu Thr
            180                 185                 190

Thr Ile Gly Phe Gly Asp Tyr Val Ala Leu Gln Lys Asp Gln Ala Leu
        195                 200                 205

Gln Thr Gln Pro Gln Tyr Val Ala Phe Ser Phe Val Tyr Ile Leu Thr
    210                 215                 220

Gly Leu Thr Val Ile Gly Ala Phe Leu
225                 230

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 16

Gly Ala Ala Val Phe
  1               5
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 17

Asn Trp Asp Phe
  1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:consensus
      peptide

<400> SEQUENCE: 18

Thr Thr Ile Gly Tyr Gly
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:consensus
      peptide

<400> SEQUENCE: 19

Gly Ile Pro Leu Thr Leu
  1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 20

Ala Val Phe Ser
  1

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence:consensus
      peptide

<400> SEQUENCE: 21

Tyr Phe Cys Phe Ile Thr Leu Ser Thr Ile Gly Phe Gly Asp Tyr Val
  1               5                  10                  15

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 22
```

Ile Leu Leu Gly Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:
      hexahistidine (His) affinity tag

<400> SEQUENCE: 23

His His His His His His
1               5

<210> SEQ ID NO 24
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 24

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly
        195                 200